(12) United States Patent
Dickerson

(10) Patent No.: US 12,186,046 B2
(45) Date of Patent: Jan. 7, 2025

(54) INSERTION LOCKOUTS FOR SURGICAL INSTRUMENTS

(71) Applicant: Cilag GmbH International, Zug (CH)

(72) Inventor: Benjamin David Dickerson, San Francisco, CA (US)

(73) Assignee: Cilag GmbH International, Zug (CH)

( * ) Notice: Subject to any disclaimer, the term of this patent is extended or adjusted under 35 U.S.C. 154(b) by 483 days.

(21) Appl. No.: 17/711,576

(22) Filed: Apr. 1, 2022

(65) Prior Publication Data

US 2023/0310101 A1    Oct. 5, 2023

(51) Int. Cl.
*A61B 34/30* (2016.01)
*A61B 34/00* (2016.01)
*A61B 34/37* (2016.01)
*A61B 17/00* (2006.01)

(52) U.S. Cl.
CPC .............. *A61B 34/37* (2016.02); *A61B 34/30* (2016.02); *A61B 34/70* (2016.02); *A61B 2017/00477* (2013.01); *A61B 2034/305* (2016.02)

(58) Field of Classification Search
None
See application file for complete search history.

(56) References Cited

U.S. PATENT DOCUMENTS

| | | | |
|---|---|---|---|
| 6,220,368 B1 * | 4/2001 | Ark .................... | A61B 17/1626 173/217 |
| 2022/0096067 A1 * | 3/2022 | Beckman ............... | A61B 17/00 |
| 2022/0249182 A1 * | 8/2022 | Definis ................ | A61B 17/128 |

* cited by examiner

*Primary Examiner* — Kennedy Schaetzle
(74) *Attorney, Agent, or Firm* — Vorys, Sater, Seymour and Pease LLP

(57) ABSTRACT

A robotic surgical tool includes a handle and an instrument driver releasably coupled to the handle, an elongate shaft extendable through the handle and the instrument driver, and a decoupler interposing the handle and the instrument driver. The decoupler includes an insertion assembly actuatable to move the shaft, an insertion transmission gear driven by the insertion assembly, and a dwell slip clutch including an input clutch gear and an output clutch gear, the dwell slip clutch being movable between collapsed and expanded states. A lockout ring extends about the decoupler housing, and a latch ring extends about the decoupler housing and is axially offset from the lockout ring. Fully retracting the shaft moves the dwell slip clutch to the compressed state to drive the output clutch gear against the lockout ring, thereby enabling latch ring to move to an unlocked position that separates the handle from the instrument driver.

23 Claims, 24 Drawing Sheets

INSERTION LOCKOUTS FOR SURGICAL INSTRUMENTS

TECHNICAL FIELD

The systems and methods disclosed herein are directed to robotic surgical tools and, more particularly to, insertion lockout mechanisms for surgical tools that incorporate a dwell slip clutch.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Various robotic systems have recently been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables (or other elongate members) that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system and thereby actively controlling the tension balance in the drive cables. Moving the drive cables articulates the end effector to desired angular positions and configurations.

Improvements to robotically-enabled medical systems will provide physicians with the ability to perform endoscopic and laparoscopic procedures more effectively and with improved ease.

SUMMARY OF THE DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

One or more embodiments describe a robotic surgical tool that includes a handle and an instrument driver releasably coupled to the handle, an elongate shaft extendable through the handle and the instrument driver, and a decoupler interposing the handle and the instrument driver. The decoupler may include an insertion assembly rotatably mounted to a decoupler housing and actuatable to move the shaft axially relative to the handle and the instrument driver, an insertion transmission gear operatively coupled to and driven by the insertion assembly, and a dwell slip clutch rotatably mounted to the decoupler housing and including an input clutch gear and an output clutch gear, the input clutch gear being operatively coupled to the insertion transmission gear such that rotation of the insertion transmission gear drives the input clutch gear, wherein the dwell slip clutch is movable between a collapsed state, where the input clutch gear directly drives the output clutch gear, and an expanded state, where the input clutch gear is rotatable relative to the output clutch gear. The robotic surgical tool may further include a lockout ring extending about the decoupler housing and engageable with the output clutch gear, and a latch ring extending about the decoupler housing and axially offset from the lockout ring, wherein fully retracting the shaft moves the dwell slip clutch to the compressed state to drive the output clutch gear against the lockout ring and thereby angularly align the latch ring with the lockout ring, and wherein, when the latch ring is angularly aligned with the lockout ring, the latch ring is movable to an unlocked position that separates the handle from the instrument driver.

One or more additional embodiments describe a method of operating a robotic surgical tool, the method including the step of releasably coupling a handle of the robotic surgical tool to an instrument driver, and the robotic surgical tool including an elongate shaft extendable through the handle and the instrument driver, a decoupler interposing the handle and the instrument driver and including an insertion assembly rotatably mounted to a decoupler housing, an insertion transmission gear operatively coupled to and driven by the insertion assembly, and a dwell slip clutch rotatably mounted to the decoupler housing and including an input clutch gear and an output clutch gear, the input clutch gear being operatively coupled to the insertion transmission gear, a lockout ring extending about the decoupler housing and engageable with the output clutch gear, and a latch ring extending about the decoupler housing and axially offset from the lockout ring. The method may further include the steps of actuating the insertion assembly and thereby moving the shaft axially relative to the handle and the instrument driver, driving the dwell slip clutch via actuation of the insertion assembly, the dwell slip clutch being movable between a collapsed state, where the input clutch gear directly drives the output clutch gear, and an expanded state, where the input clutch gear is rotatable relative to the output clutch gear, retracting the shaft and thereby transitioning the dwell slip clutch to the compressed state where the output clutch gear drives against the lockout ring, rotating the lockout ring with the output cutch gear and thereby angularly aligning the lockout ring with latch ring, and moving the latch ring to an unlocked position once the latch ring is angularly aligned with the lockout ring, and thereby separating the handle from the instrument driver.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance, to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto, as such concepts may have applicability throughout the entire specification.

A. Robotic System—Cart.

Figure 1:
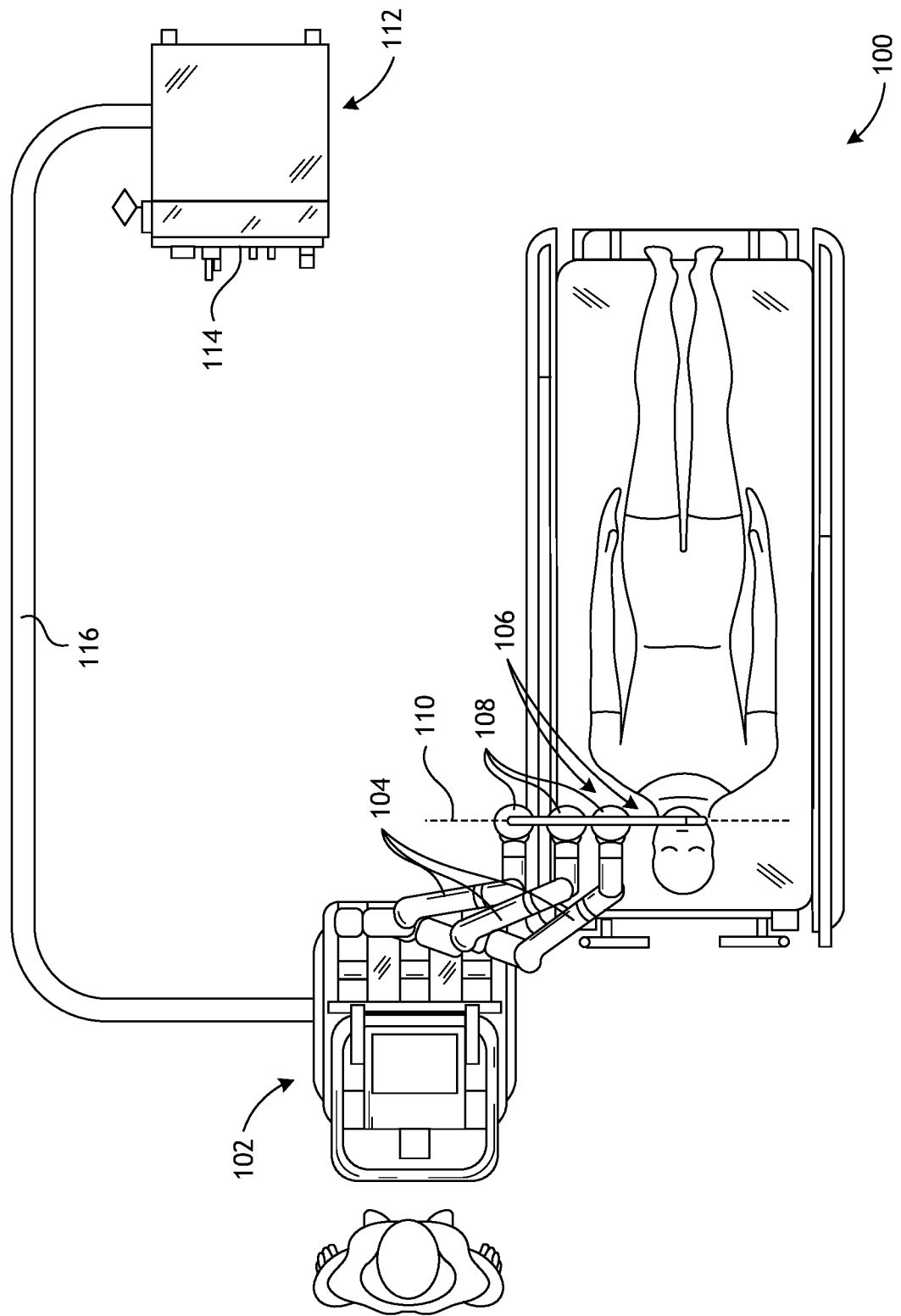
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastro-intestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or repositioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
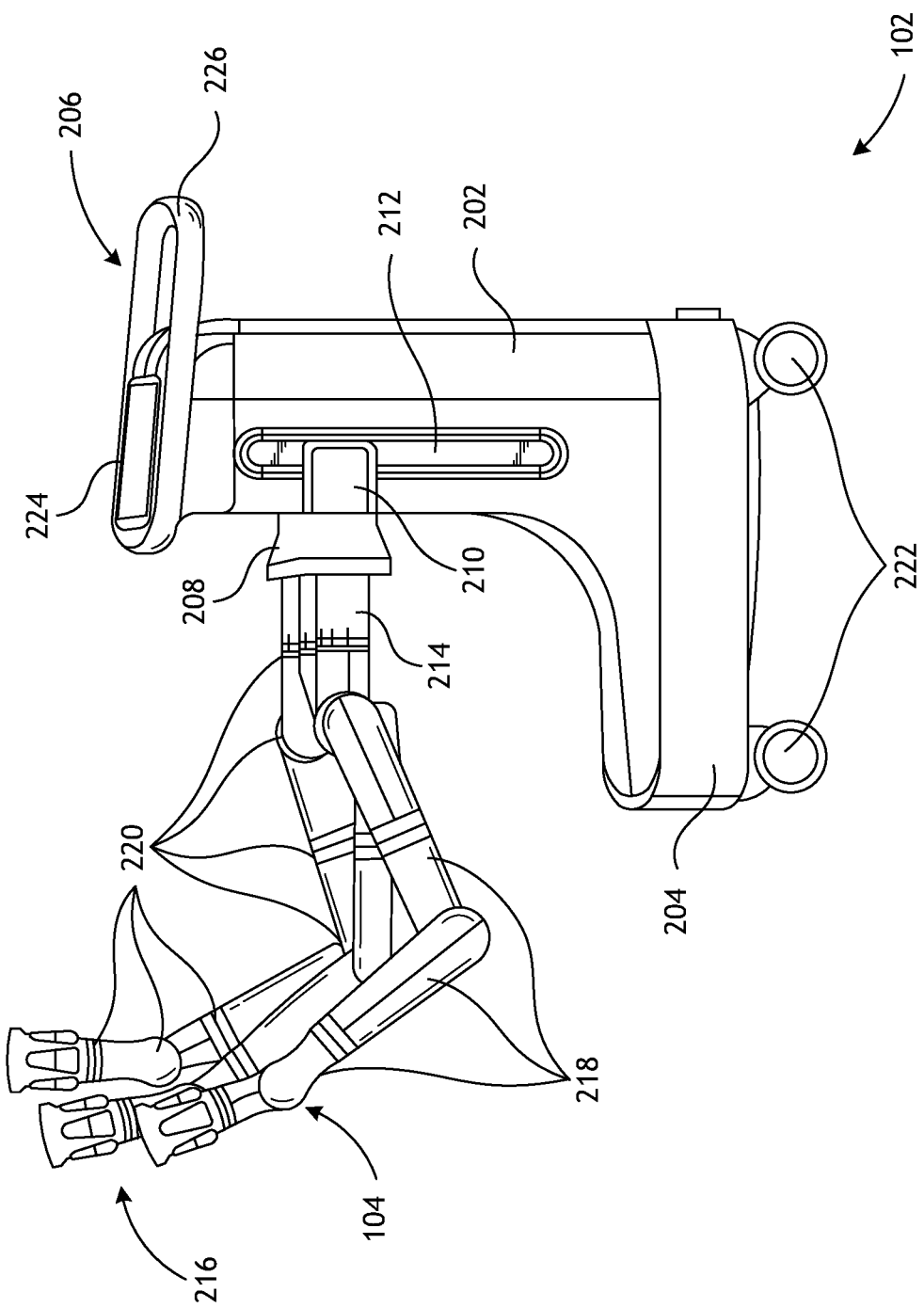
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, which are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, the carriage 208, and the arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure. After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
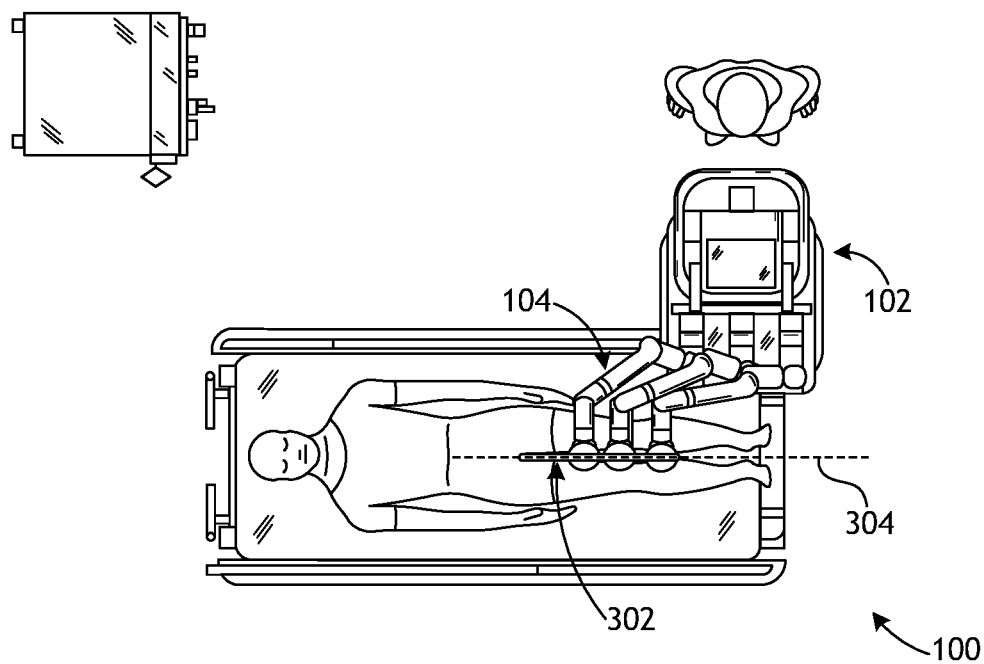
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
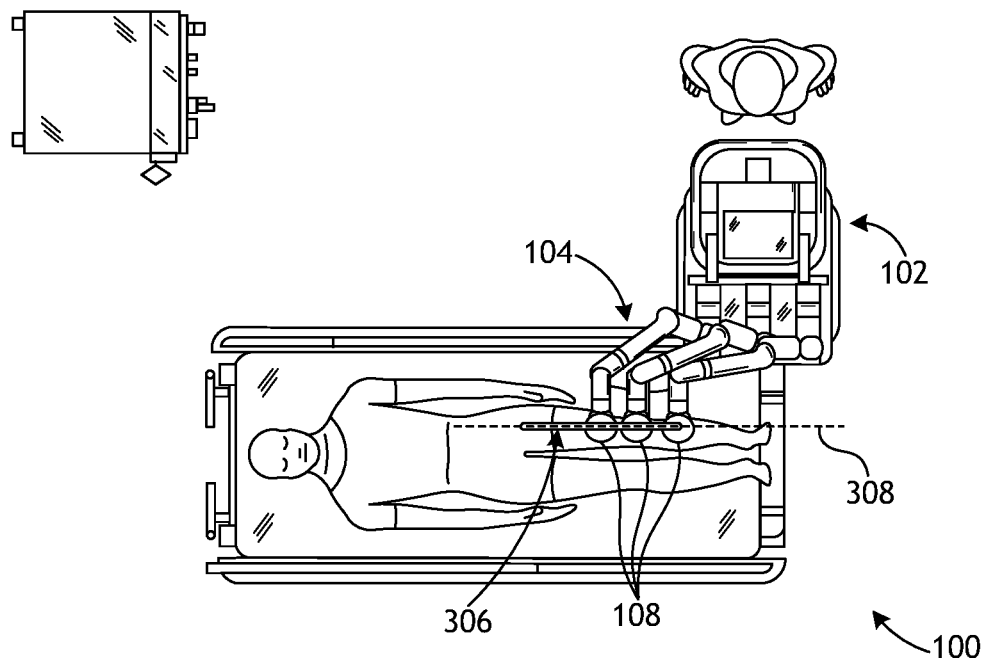
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
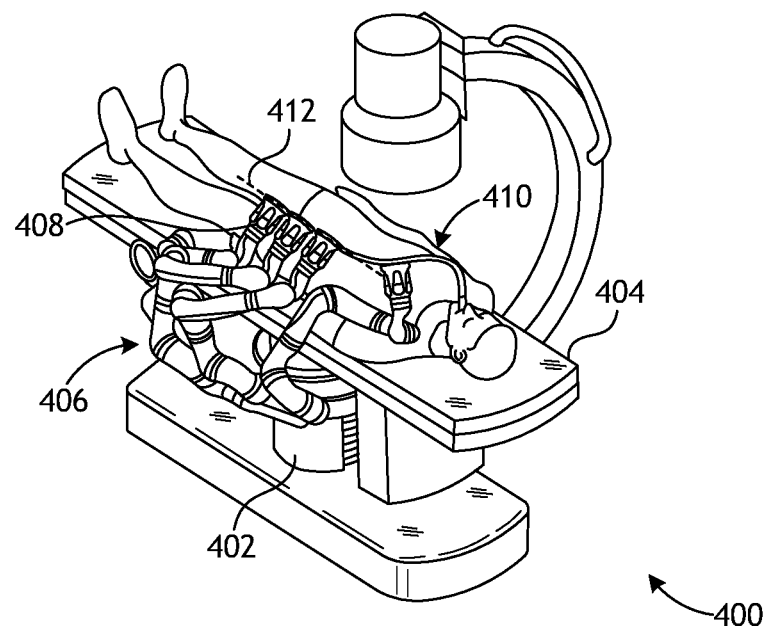
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
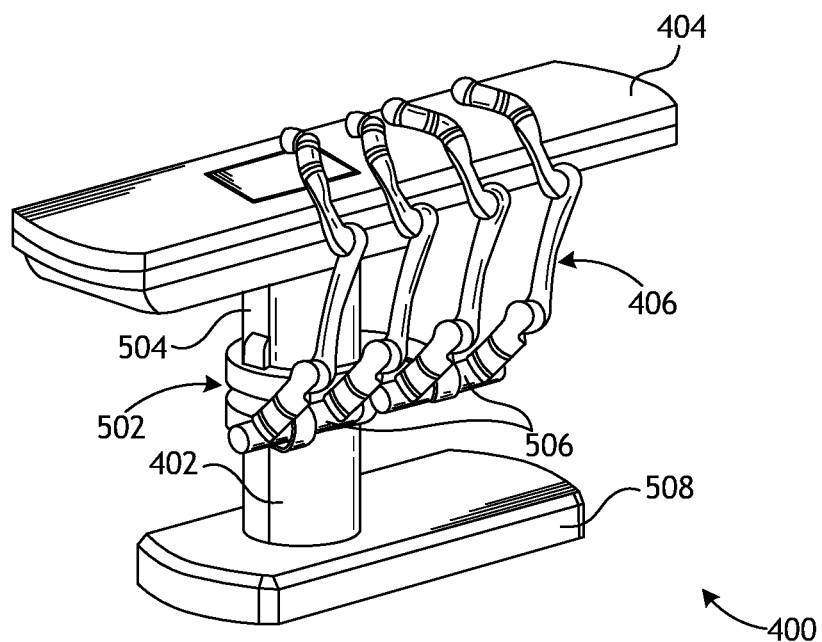
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
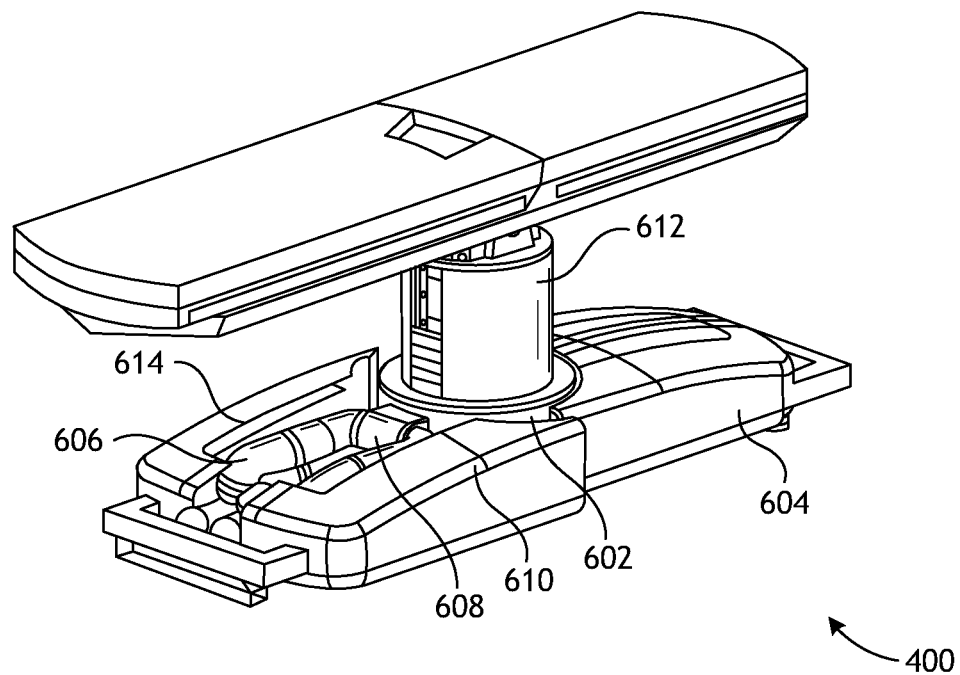
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
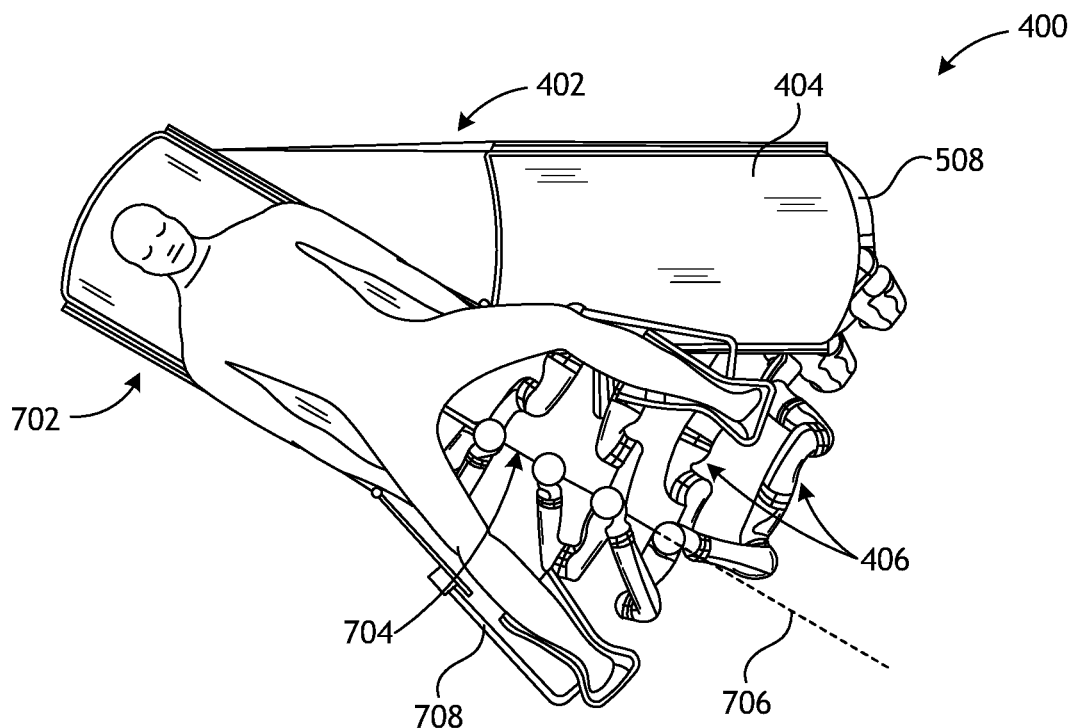
FIG. 7A illustrates an embodiment of a table-based robotic system configured for a ureteroscopy procedure.
Figure 7B:
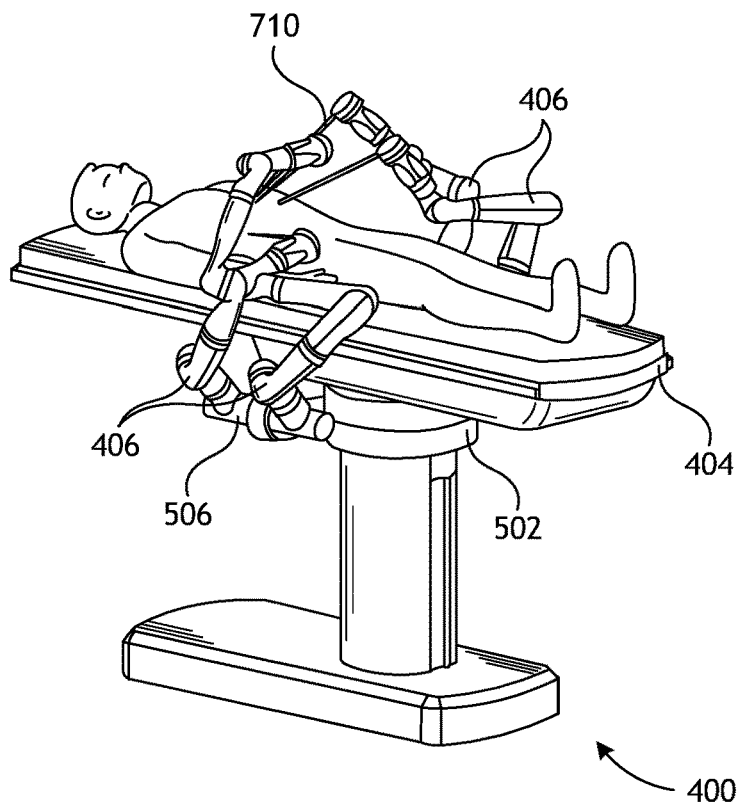
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
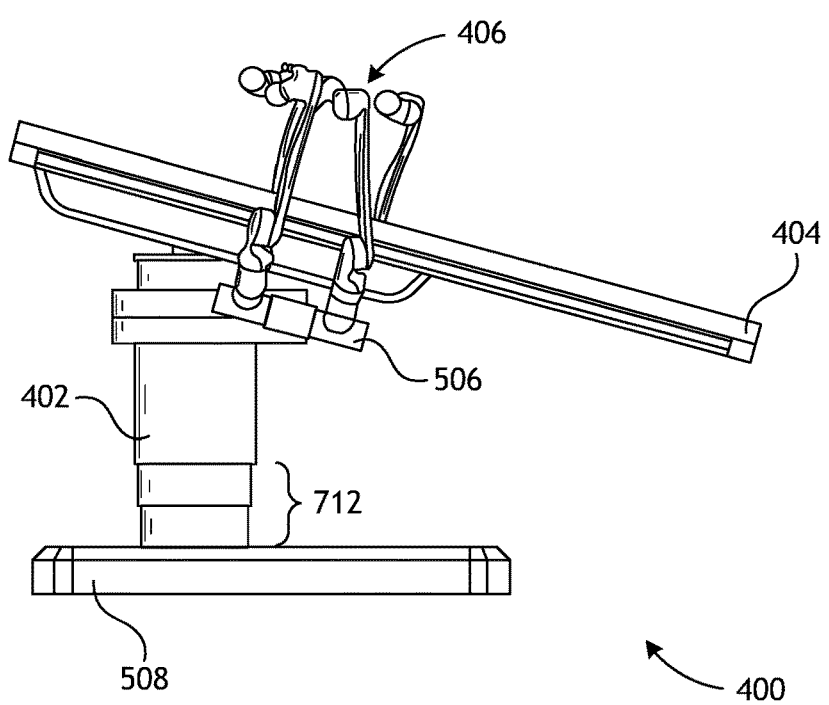
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
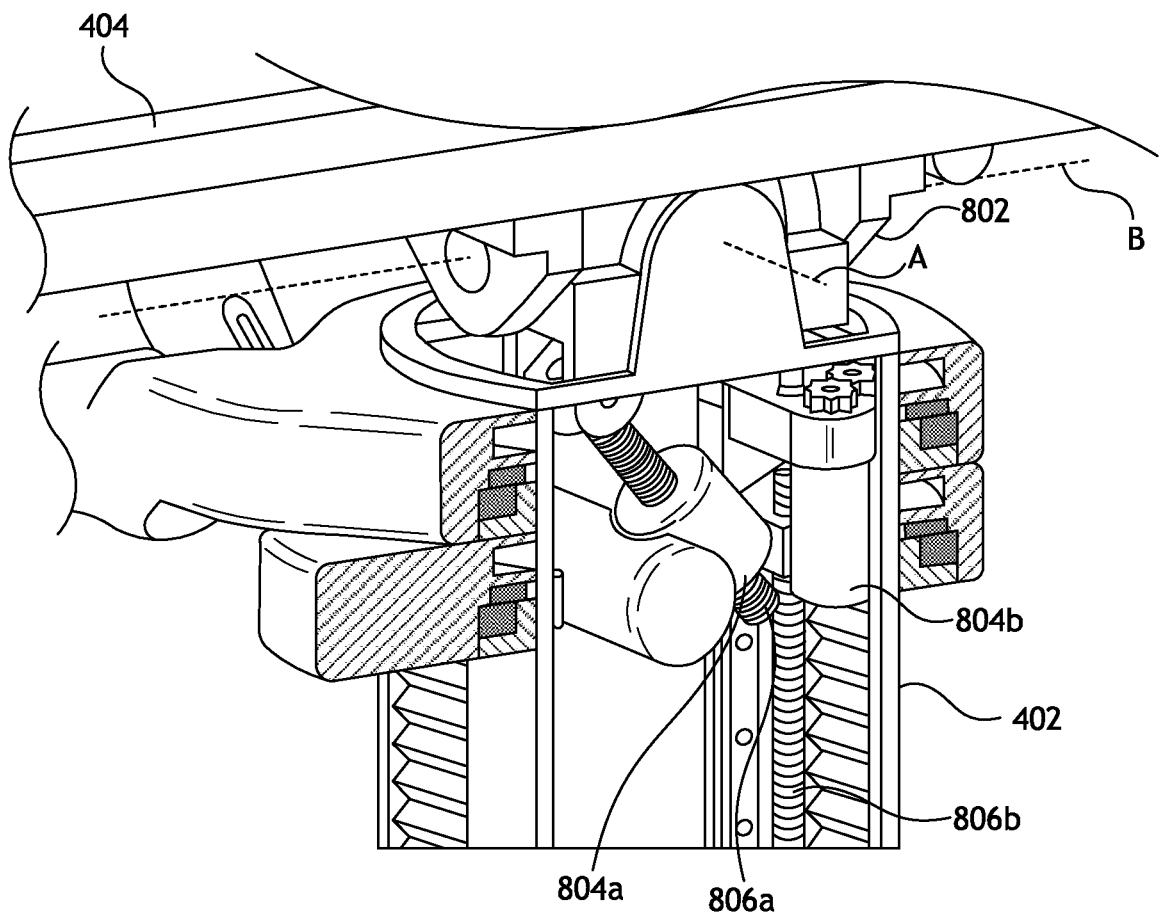
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
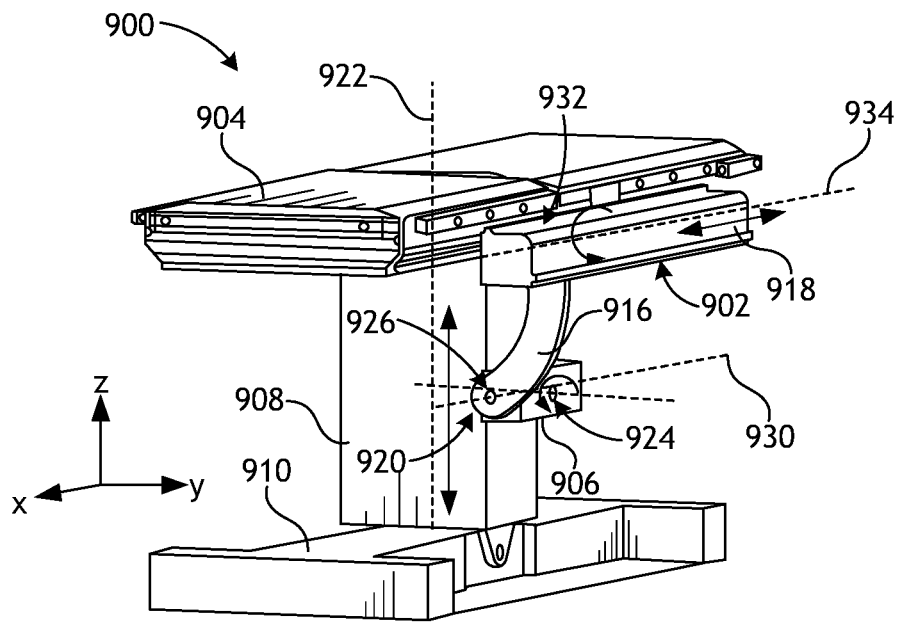
FIG. 9A illustrates an alternative embodiment of a table-based robotic system.
Figure 9B:
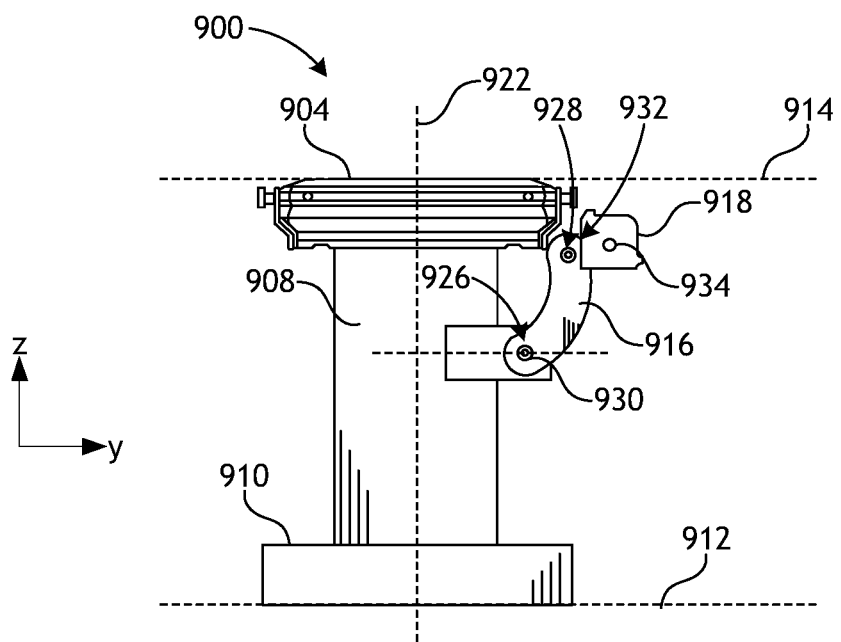
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
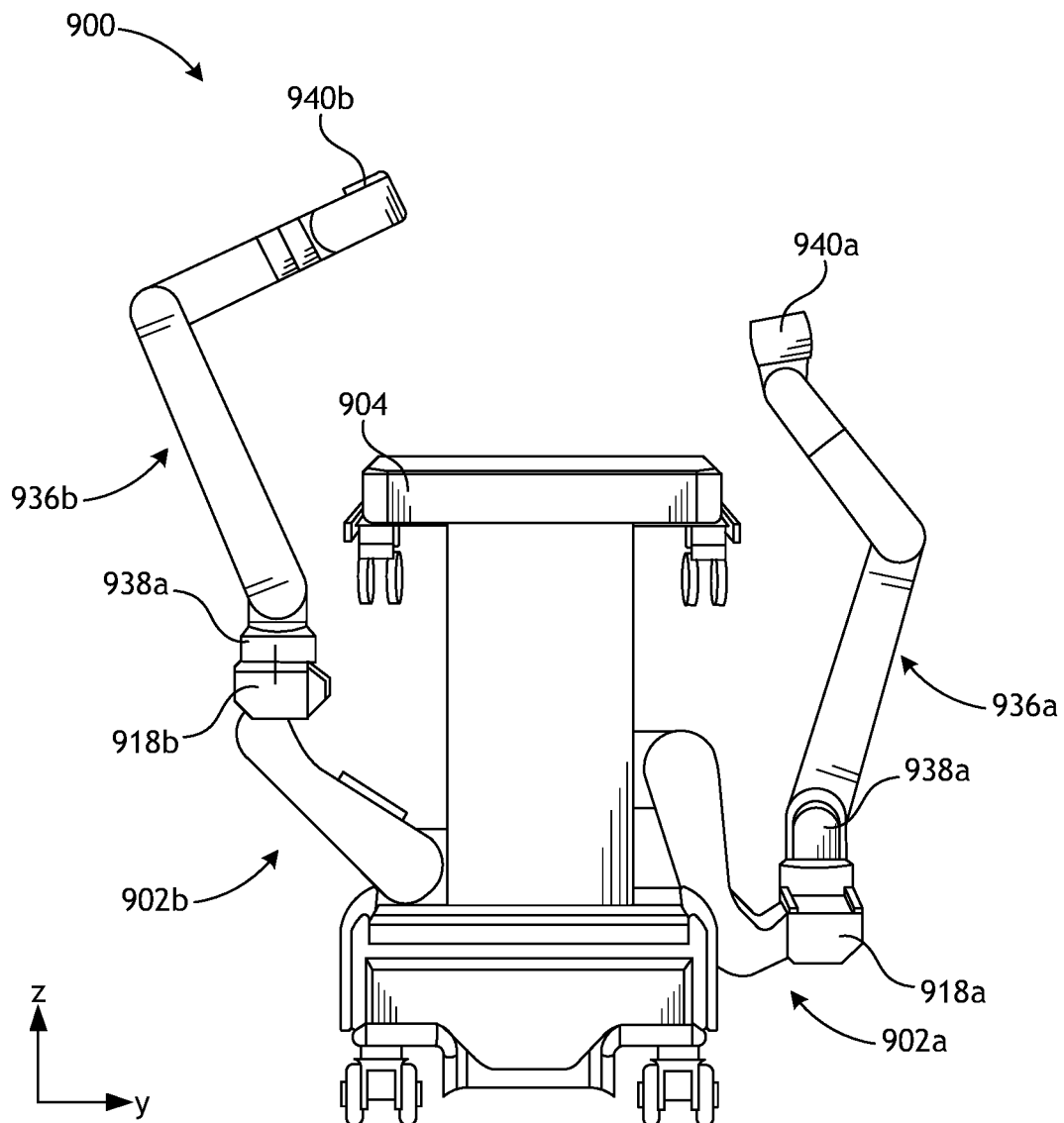
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
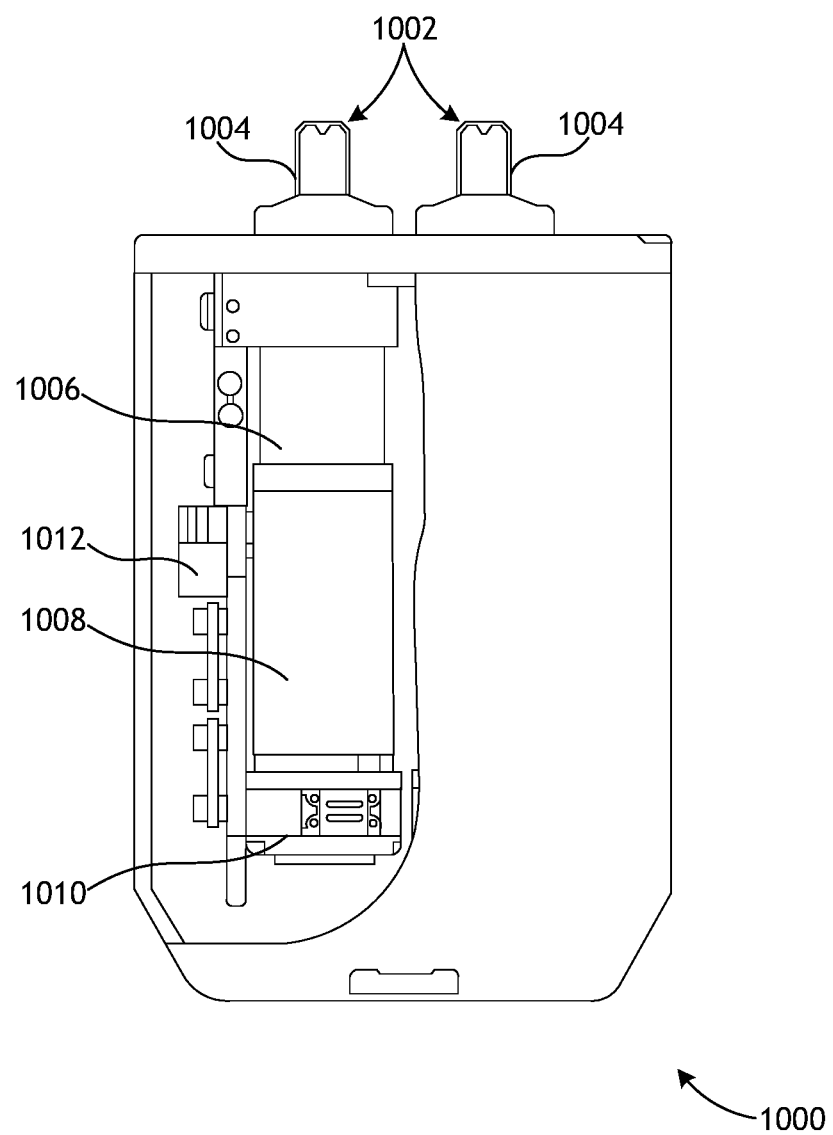
FIG. 10 illustrates an exemplary instrument driver.

FIG. 10 illustrates an example instrument driver 1000, according to one or more embodiments. Positioned at the distal end of a robotic arm, the instrument driver 1000 includes one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independently controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
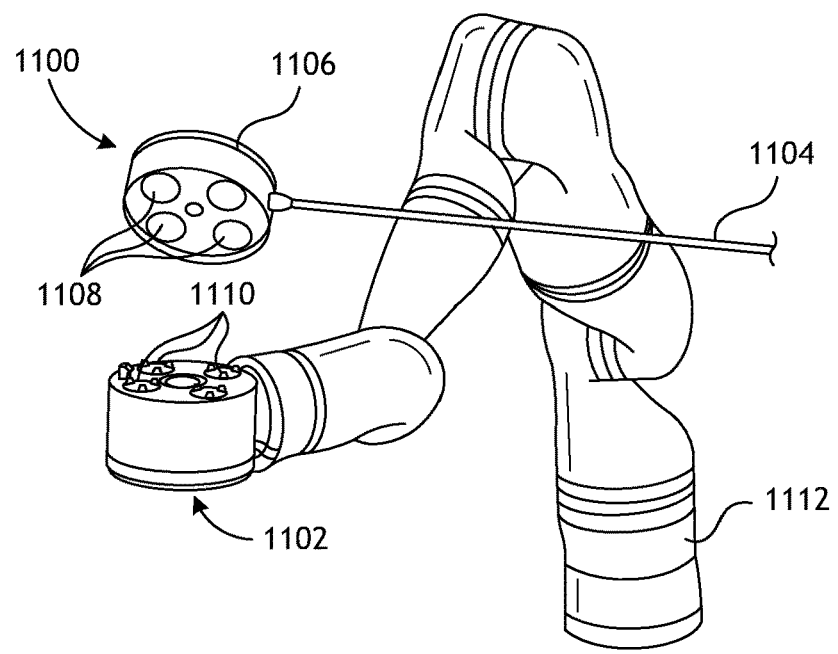
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
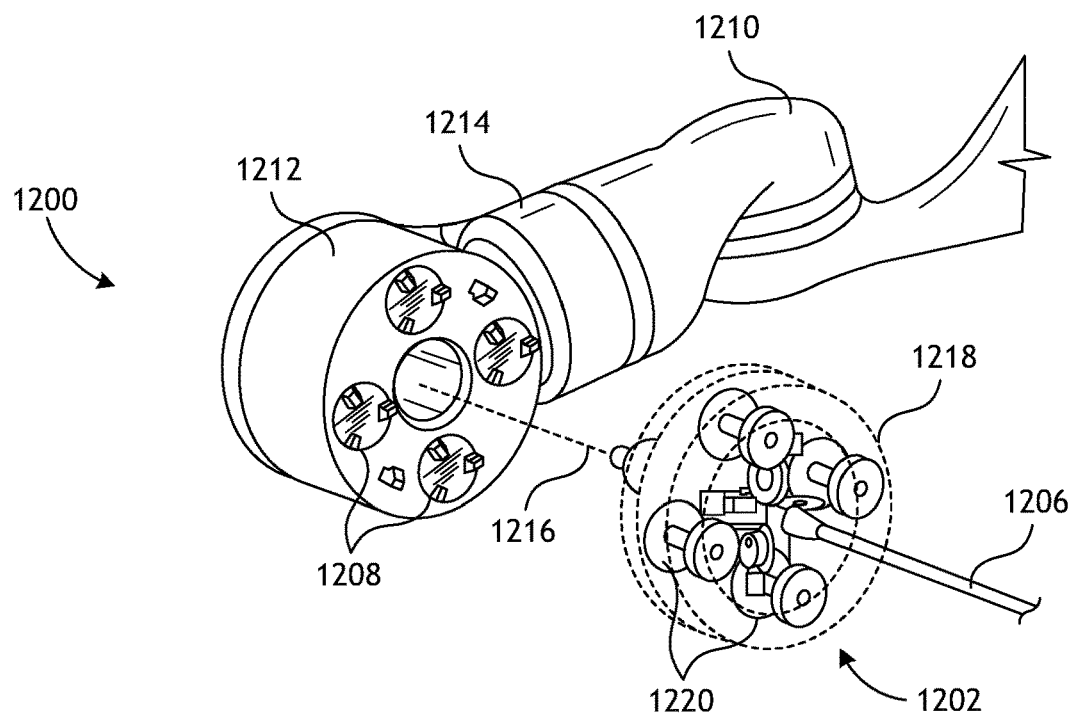
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
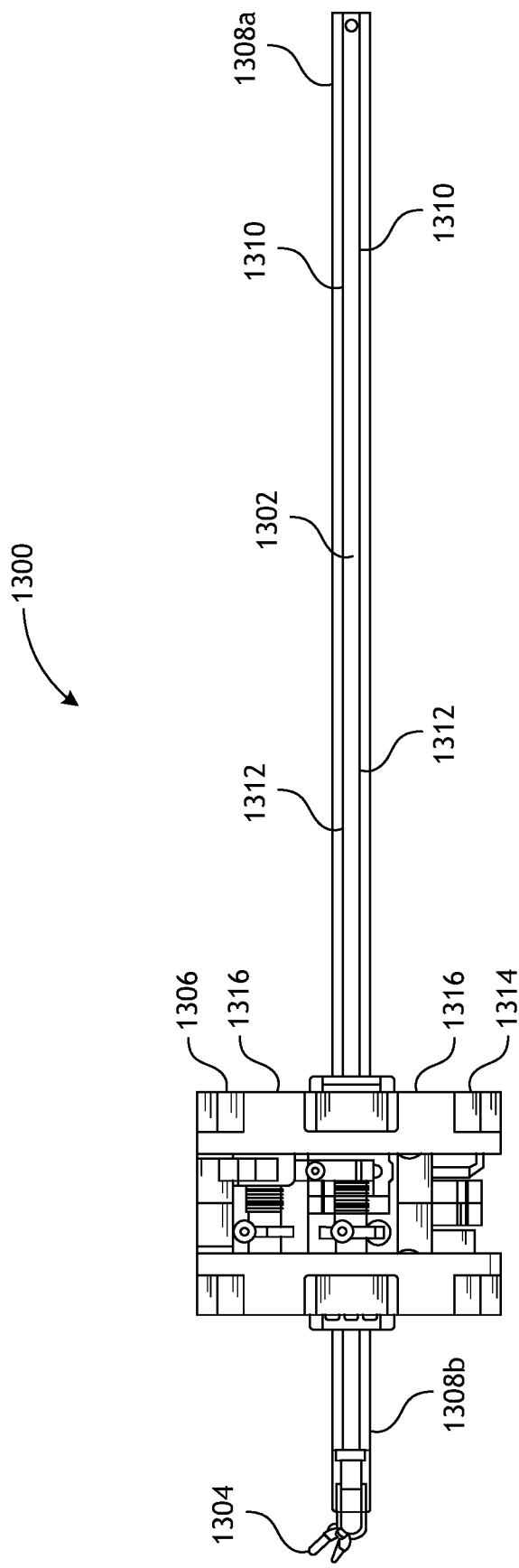
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308*a* and a distal portion 1308*b*. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument 1300, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
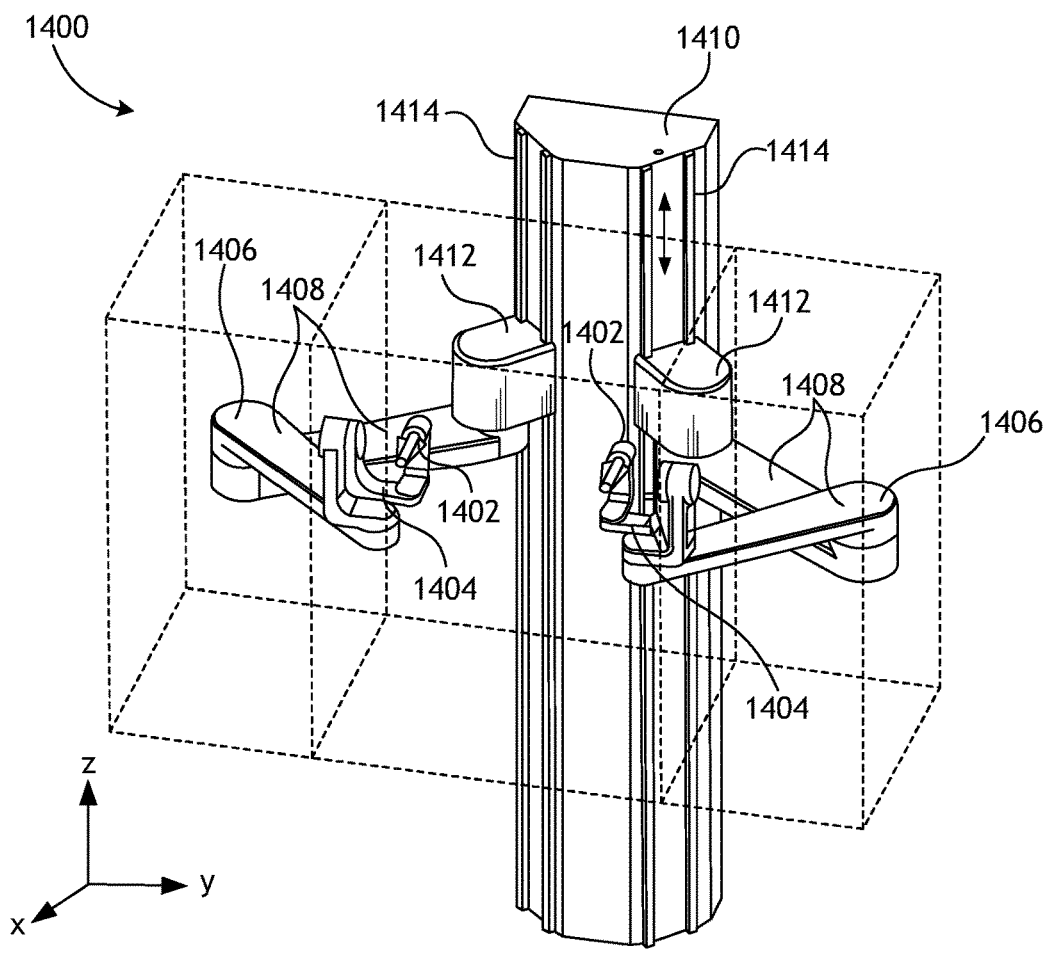
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
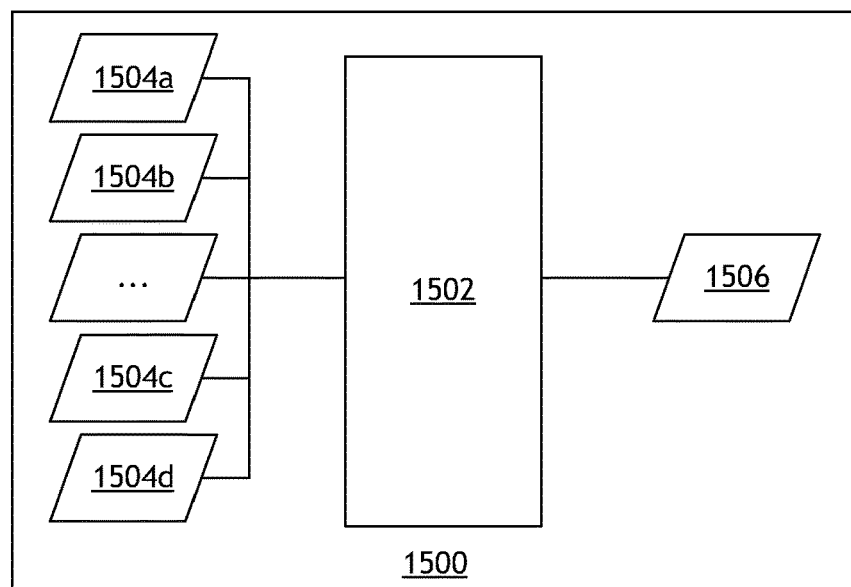
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504*b* to enable computer vision-based tracking of the medical instrument (e.g., an endoscope or an instrument advance through a working channel of the endoscope). For example, using the preoperative model data 1504*a*, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504*a* that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504*b* to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504*c*. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504*d* may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504*a-d* in combination(s). In some cases, such a combination may use a probabilistic approach where the localization module 1502 assigns a confidence weight to the location determined from each of the input data 1504*a-d*. Thus, where the EM data 1504*c* may not be reliable (as may be the case where there is EM interference) the confidence of the location determined by the EM data 1504*c* can be decrease and the localization module 1502 may rely more heavily on the vision data 1504*b* and/or the robotic command and kinematics data 1504*d*.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Description.

Figure 16:
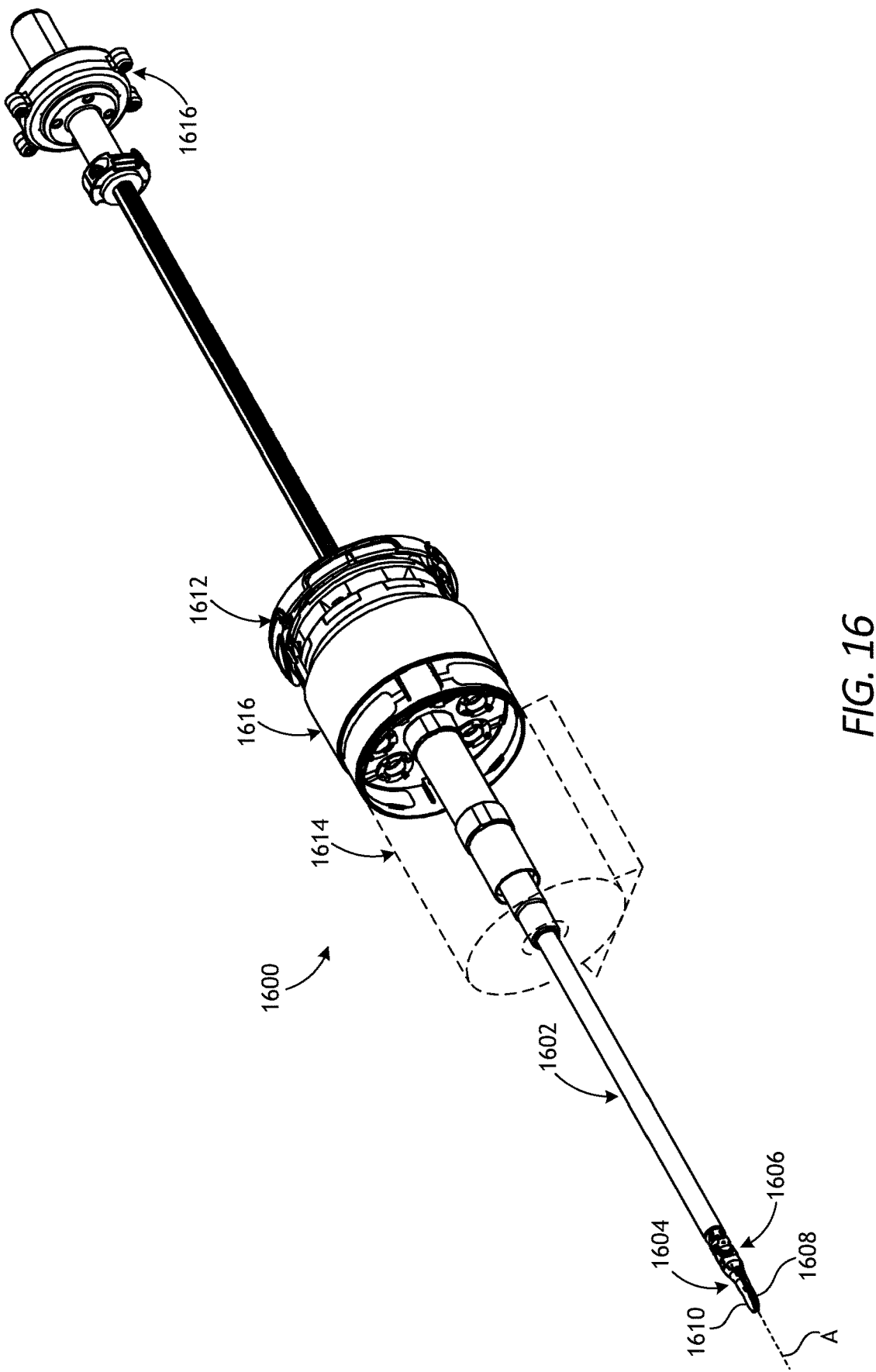
FIG. 16 is an isometric view of another example surgical tool that may incorporate some or all of the principles of the present disclosure.

FIG. 16 is an isometric view of an example surgical tool 1600 that may incorporate some or all of the principles of the present disclosure. The surgical tool 1600 may be similar in some respects to any of the surgical tools and medical instruments described above with reference to FIGS. 11-13 and, therefore, may be used in conjunction with a robotic surgical system, such as the robotically-enabled systems 100, 400, and 900 of FIGS. 1-9C. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602. In some embodiments, the wrist 1606 may be omitted, without departing from the scope of the disclosure.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding FIG. and the downward or lower direction being toward the bottom of the corresponding figure.

The surgical tool 1600 can have any of a variety of configurations capable of performing one or more surgical functions. In the illustrated embodiment, the end effector 1604 comprises a vessel sealer capable of grasping onto tissue or vessels. The end effector 1604 includes opposing jaws 1608, 1610 configured to move (articulate) between open and closed positions. Alternatively, the end effector 1604 may comprise other types of instruments with opposing jaws such as, but not limited to, a surgical stapler, a tissue grasper, surgical scissors, clip appliers, needle drivers, a babcock including a pair of opposed grasping jaws, bipolar jaws (e.g., bipolar Maryland grasper, forceps, a fenestrated grasper, etc.), etc.

One or both of the jaws 1608, 1610 may be configured to pivot to actuate the end effector 1604 between open and closed positions. In the illustrated example, both jaws 1608, 1610 simultaneously move to pivot the jaws 1608, 1610 between an open, unclamped position and a closed, clamped position and are thus referred to as "bifurcating" jaws. In other embodiments, however, only one of the jaws 1608, 1610 may be rotatable (pivotable) relative to the opposing jaw to actuate the end effector 1604 between the open and closed positions.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis Ai of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The end effector 1604 is depicted in FIG. 16 in the unarticulated position where the longitudinal axis of the end effector 1604 is substantially aligned with the longitudinal axis Ai of the shaft 1602, such that the end effector 1604 is at a substantially zero angle relative to the shaft 1602. When articulated, the longitudinal axis of the end effector 1604 becomes angularly offset from the longitudinal axis Ai such that the end effector 1604 is oriented at a non-zero angle relative to the shaft 1602.

Still referring to FIG. 16, the surgical tool 1600 may include a drive housing or "handle" 1612, and the shaft 1602 extends longitudinally through the handle 1612. The handle 1612 houses an actuation system designed to facilitate articulation of the wrist 1606 and actuation (operation) of the end effector 1604 (e.g., clamping, firing, rotation, articulation, energy delivery, etc.). As discussed in more detail below, the handle 1612 may include and otherwise house a plurality of drive gears that are actuatable to drive against and axially move (translate) a plurality of sliding rack gears nested within corresponding longitudinal channels defined along all or a portion of the shaft 1602. In some embodiments, the distal end of each rack gear is attached to distal cables that extend to the end effector 1604 or the wrist 1606 at the distal end of the shaft 1602, and the proximal end of the each rack gear is attached to proximal cables that extend to a proximal end of the shaft 1602. In other embodiments, however, the distal end of one or more of the rack gears may be directly attached to portions of the end effector 1604 or the wrist 1606 to enable a push-pull translation action (e.g., in the case of push/pull rods).

Selective actuation of one or more of the sliding rack gears, for example, may cause the end effector 1604 to articulate (pivot) relative to the shaft 1602 at the wrist 1606. Selective actuation of one or more additional sliding rack gears may cause the end effector 1604 to actuate (operate). Actuating the end effector 1604 depicted in FIG. 16 may entail closing and/or opening the jaws, 1608, 1610 and thereby enabling the end effector 1604 to grasp (clamp) onto tissue. In embodiments where the end effector 1604 comprises a vessel sealer, once tissue is grasped or clamped between the opposing jaws 1608, 1610, actuating the end effector 1604 may further include "firing" the end effector 1604, which may refer to causing a cutting element or knife (not visible) to advance distally within a slot or "guide track" defined in the first jaw 1610. As it moves distally within the guide track, the knife transects tissue grasped between the opposing jaws 1608, 1610.

The actuation system housed within the handle 1612 may further be designed to move the shaft 1602 relative to (through) the handle 1612 and along the longitudinal axis $A_1$. More particularly, the actuation system may also include a drive gear actuatable to engage a rack gear defined on the shaft 1602 itself; i.e., a "shaft rack gear". When the drive gear drives against the shaft rack gear, the shaft 1602 along with the nested sliding rack gears are moved (translated) axially relative to the handle 1612, as indicated by the arrows B. Moreover, as the shaft 1602 moves, the end effector 1604 and the wrist 1606 are simultaneously advanced or retracted, depending on the driving direction.

The handle 1612 may be operatively coupled to an instrument driver 1614 of a robotic surgical system. The instrument driver 1614 may be similar in some respects to the instrument drivers 1102, 1200 of FIGS. 11 and 12, respectively, and therefore may be best understood with reference thereto. Similar to the instrument drivers 1102, 1200, for example, the instrument driver 1614 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1614.

The handle 1612 includes a plurality of rotatable drive inputs (not visible) that can be driven by a corresponding plurality of drive outputs (not visible) of the instrument driver 1614. Each drive input is actuatable to independently drive (actuate) various portions of the actuation system housed within the handle 1612 and thereby operate the surgical tool 1600, as generally described above. The number of drive outputs will generally be the same as the number of drive inputs, but the instrument driver 1614 can have additional drive outputs, without departing from the scope of the disclosure. Movement (rotation) of a given drive output correspondingly moves (rotates) an associated drive input and thereby operates the surgical tool 1600. More specifically, actuation of the drive inputs drives the various drive gears mentioned above, which may be arranged to drive the corresponding rack gears, and moving the rack gears causes the end effector 1604 to articulate and/or actuate (operate) and the shaft 1602 to axially move (translate) relative to the handle 1612.

In the illustrated embodiment, a decoupler subassembly or "decoupler" 1616 is arranged between and otherwise interposes the handle 1612 and the instrument driver 1614. Among other functions described herein, the decoupler 1616 transfers torque from the drive outputs of the instrument driver 1614 to the drive inputs of the handle 1612, and thus operates as a type of torque transfer apparatus. Once the drive outputs are operatively and indirectly coupled to corresponding drive inputs via the decoupler 1616, rotational torque may be transferred from the drive outputs to the corresponding drive inputs through (via) the decoupler 1616, thus being able to operate the handle 1612. As discussed in more detail below, the decoupler 1616 may also be advantageous in transferring insertion motion (e.g., movement of the shaft 1602) to all the drive inputs, thus allowing one robot motor to control insertion of the surgical tool 1600, while allowing the other motors of the instrument driver 1614 to drive the sliding rack gears independent of insertion.

Lastly, in some embodiments, the surgical tool 1600 may include a tailpiece 1616 arranged at the proximal end of the shaft 1602. In some embodiments, the tailpiece 1616 may comprise a mechanical device that provides a means for manually controlling the end effector 1604 and/or the wrist 1606. The tailpiece 1616 can be designed to hold a mechanism referred to as a "pantograph" or a "pantograph button". The pantograph essentially acts as a manually manipulatable mirror to the wrist 1606 and ensures that the system maintains tension in the surgical tool 1600 when disconnected from the instrument driver 1614 (e.g., the robot).

Figure 17:
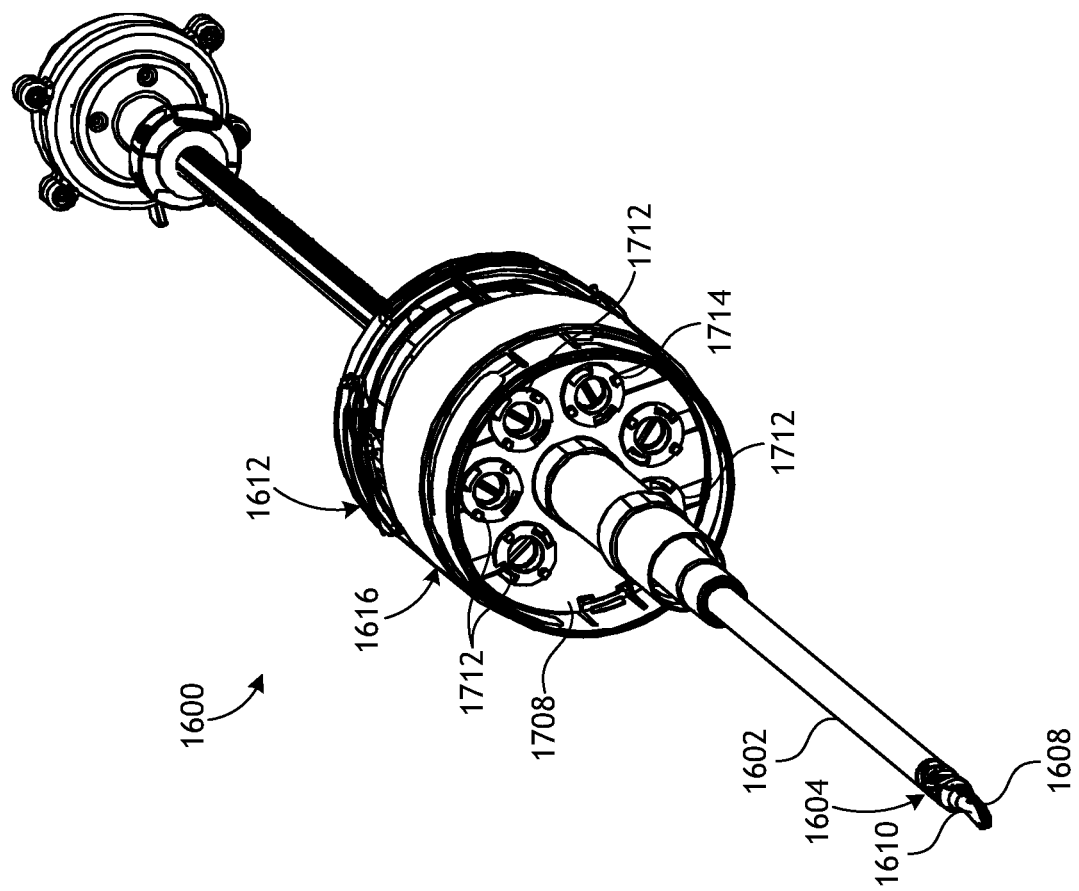
FIG. 17 depicts separated isometric end views of the instrument driver and the surgical tool of FIG. 16.
Figure 17:
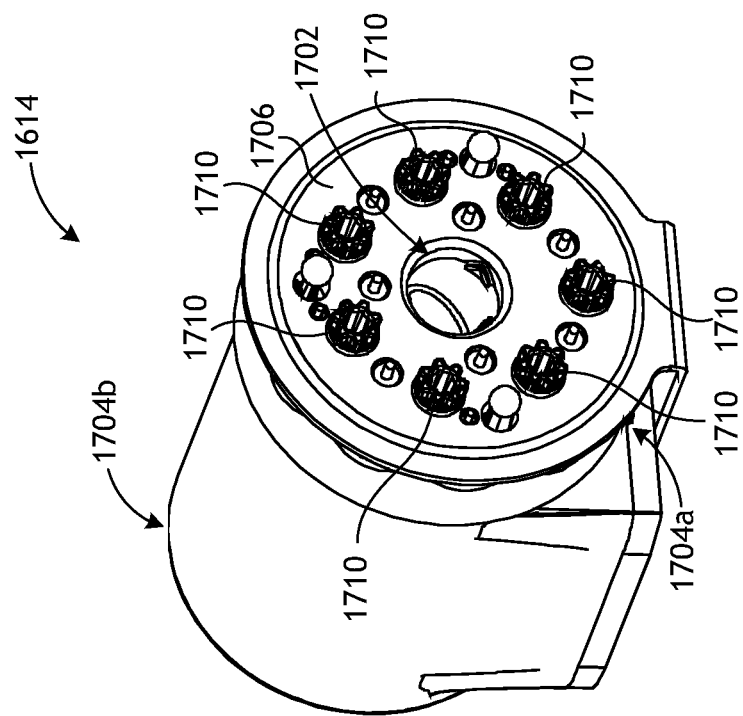

FIG. 17 depicts separated isometric end views of the instrument driver 1614 and the surgical tool 1600 of FIG. 16. With the jaws 1608, 1610 closed, the shaft 1602 and the end effector 1604 can penetrate the instrument driver 1614 by extending through a central aperture 1702 defined longitudinally through the instrument driver 1614 between first and second ends 1704a and 1704b. A drive interface 1706 is provided at the first end 1704a of the instrument driver 1614 and is matable with a driven interface 1708 provided on the distal end of the handle 1612, or in embodiments that include the decoupler 1616, the distal end (bottom) of the decoupler 1616. The drive and driven interfaces 1706, 1708 may be configured to mechanically, magnetically, and/or electrically couple the handle 1612 to the instrument driver 1614.

The instrument driver 1614 includes a plurality of drive outputs 1710 that extend through the drive interface 1706. In embodiments including the decoupler 1616, the drive outputs 1710 are configured to mate with corresponding differential inputs 1712 provided at the distal end of the decoupler 1616. At least one of the differential inputs 1712 may be an insertion input 1714 operable to facilitate axial translation of the shaft 1602. The number of drive outputs 1710 will generally be the same as the number of differential and insertion inputs 1712, 1714, but it is contemplated herein that the instrument driver 1614 can have additional drive outputs, without departing from the scope of the disclosure. In embodiments where the surgical tool 1600 omits the decoupler 1616, the drive outputs 1710 may be configured to mate with corresponding drive inputs (not shown) provided on the handle 1612.

The drive outputs 1710 may define splines, protrusions, or other mechanical features designed to mate with corresponding receptacles of the differential and insertion inputs 1712, 1714, or vice versa. One of the drive outputs 1710 may be configured to mate with the insertion input 1714; this drive output 1710 is referred to herein as a "shaft drive output." Once properly mated, the differential and insertion inputs 1712, 1714 will share axes of rotation with the corresponding drive outputs 1710 to allow the transfer of rotational torque from the drive outputs 1710 to the corresponding differential inputs 1712, 1714. In some embodiments, each drive output 1710 may be spring loaded and otherwise biased to spring outwards away from the drive interface 1706. Each drive output 1710 may be capable of partially or fully retracting into the drive interface 1706.

Figure 18A:
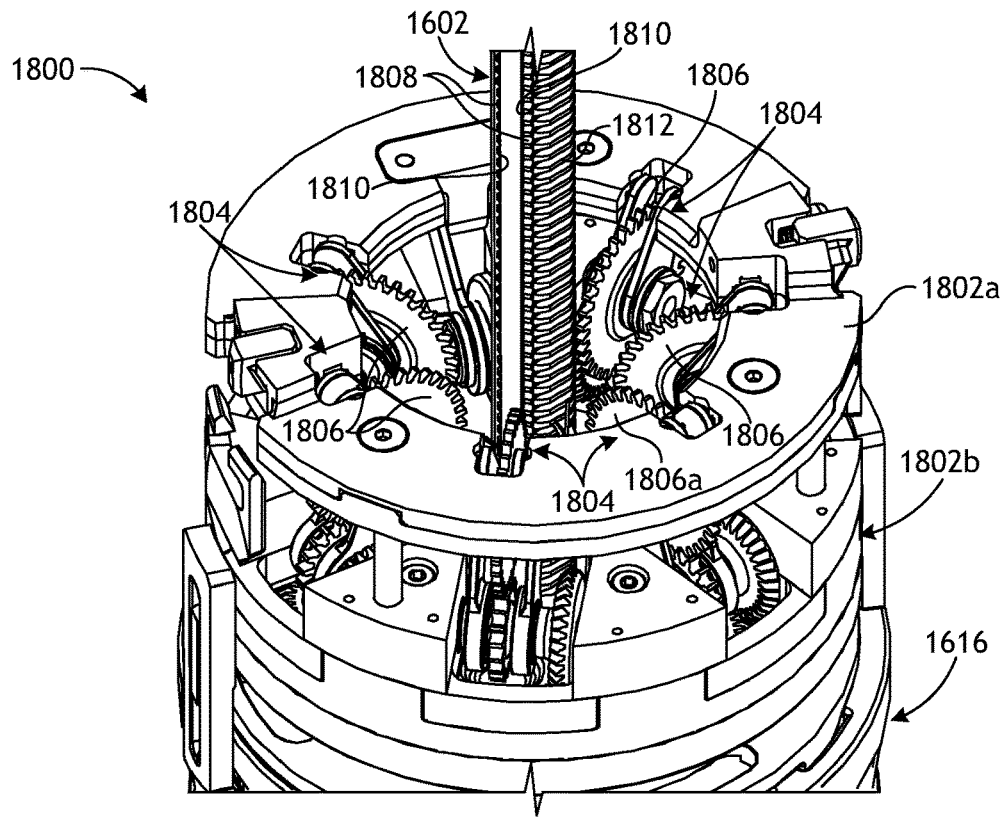
FIGS. 18A and 18B are isometric open (disengaged) and closed (engaged) views, respectively, of an example actuation system, according to one or more additional embodiments.
Figure 18B:
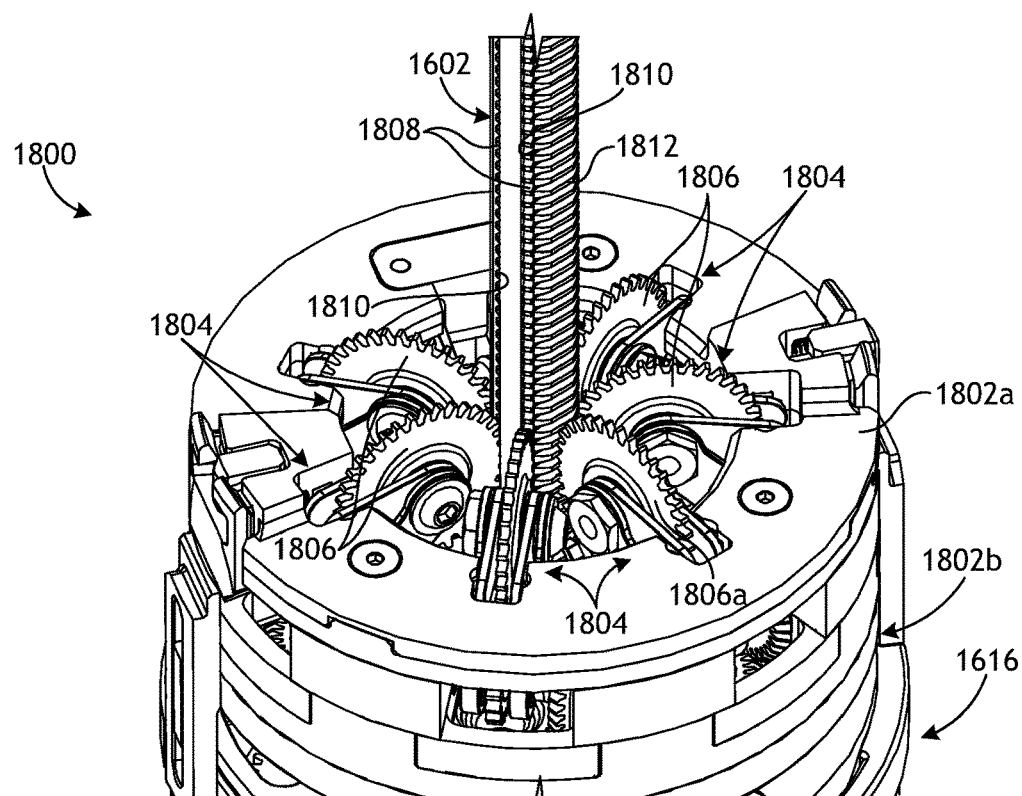

FIGS. 18A and 18B are isometric open (disengaged) and closed (engaged) views, respectively, of an example actuation system 1800, according to one or more embodiments. The actuation system 1800, also referred to as an axle redirect assembly, may be housed within the handle 1612 and operable to actuate (operate) the end effector 1604 (FIG. 16), articulate the wrist 1606 (FIG. 16), and axially move (translate) the shaft 1602 relative to (i.e., through) the handle 1612. Several parts and structural elements of the handle 1612, such as the outer housing, are omitted from FIGS. 18A-18B to enable ease of viewing of the actuation system 1800 for purposes of discussion.

As illustrated, the actuation system 1800 may include a first or "upper" mounting assembly 1802a and a second or "bottom" mounting assembly 1802b. In the depicted embodiment, the mounting assemblies 1802a,b are vertically offset rings concentrically arranged about the shaft 1602. The upper mounting assembly 1802a is a translating ring that moves relative to the lower mounting assembly 1802b to allow and enable assembly of the instrument shaft 1602 to the actuation system 1800 and the decoupler 1616. The bottom mounting assembly 1802b is the base of the axle redirect assembly or actuation system 1800. A plurality of spur linkage subassemblies 1804 are pivotably mounted to the mounting assemblies 1802a,b and configured to pivot between a first or "disengaged" position, as shown in FIG. 18A, and a second or "engaged" position, as shown in FIG. 18B.

Each spur linkage subassembly 1804 includes a corresponding drive gear 1806 arranged to drive against an adjacent sliding rack gear 1808 (two visible in FIGS. 18A-18B). Each sliding rack gear 1808 is movably nested within a corresponding longitudinal channel 1810 defined along all or a portion of the shaft 1602. In the illustrated embodiment, the drive gears 1806 are depicted as spur gears with teeth matable with corresponding teeth defined on the opposing sliding rack gear 1808. Accordingly, the drive gears 1806 may alternatively be referred to herein as "spur" gears, and operation of the spur gears 1806 and corresponding sliding rack gears 1808 may conform to known rack-and-pinion operation. Driving a given sliding rack gear 1808 will urge the sliding rack gear 1808 to move (slide) within its corresponding longitudinal channel 1810, and moving the sliding rack gear 1808 within the channel 1810 may actuate (operate) the end effector 1604 (FIG. 16) and/or articulate the wrist 1606 (FIG. 16).

The rack gears 1808 may prove advantageous over cable-based systems since they have a much larger cross-sectional area than cables, which equates to a greater stiffness as compared to cables. Consequently, the performance of the tool can be more robust and predictable. Moreover, the rack gears 1808 enable the driving of instrument end effectors that do not use cables, such as push/pull rods that are often used in certain designs, such as vessel sealers and staplers.

One of the drive gears is indicated in FIGS. 18A-18B as a shaft drive gear 1806a, and is arranged to drive against an adjacent shaft rack gear 1812. The shaft rack gear 1812 may form part of and may otherwise be defined along all or a portion of the outer surface of the shaft 1602. Driving the shaft drive gear 1806a against the shaft rack gear 1812 will cause the shaft 1602 to move (translate) axially relative to (i.e., through) the handle 1612 (FIG. 16).

Figure 19:
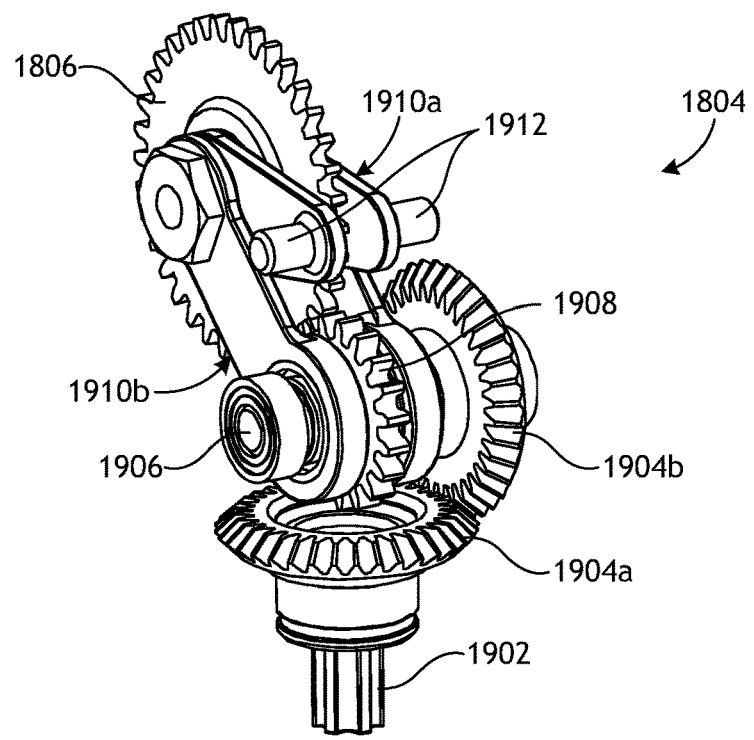
FIG. 19 is an isometric view of an example spur linkage subassembly, according to one or more embodiments.

Referring briefly to FIG. 19, illustrated is an isometric view of an example spur linkage subassembly 1804, according to one or more embodiments. As illustrated, the spur linkage subassembly 1804 includes a rotatable drive input 1902, which, in some embodiments, can be driven by one of the drive outputs 1710 (FIG. 17) of the instrument driver 1614 (FIGS. 16-17). In embodiments that include the decoupler 1616 (FIG. 16), however, a transmission differential or differential assembly provided by the decoupler 1616 will axially interpose the drive input 1902 and a corresponding drive output 1710, as generally described herein. In such embodiments, any rotational torque provided by a given drive output 1710 will be transferred to the corresponding drive input 1902 via a corresponding transmission differential of the decoupler 1616.

A gear train including one or more intermediate gears may interpose the drive input 1902 and the corresponding drive gear 1806, such that rotating the drive input 1902 will cause the corresponding drive gear 1806 to rotate. Those skilled in the art will readily appreciate that this gear train can assume a variety of configurations. In the illustrated embodiment, for example, the gear train includes mating bevel gears, shown as a bevel drive gear 1904a arranged to drive a bevel driven gear 1904b. The bevel drive gear 1904a may be coupled to or otherwise form part of the drive input 1902 such that rotation of the drive input 1902 correspondingly rotates the bevel drive gear 1904a. In some embodiments, the bevel driven gear 1904b may be mounted to an axle 1906 configured to be rotatably mounted to the lower mounting assembly 1802b (FIGS. 18A-18B). A spur gear 1908 may also be mounted to the axle 1906 and axially offset from the bevel driven gear 1904b. In at least one embodiment, however, the spur gear 1908 may be coupled to or otherwise form part of the bevel driven gear 1904b. In either scenario, rotation of the bevel driven gear 1904b will cause the spur gear 1908 to correspondingly rotate, and the spur gear 1908 may be arranged to drive the drive gear 1806.

The intermeshed bevel gears 1904a,b facilitate the directional change required in the handle 1612 (FIGS. 18A-18B). More specifically, the bevel gears 1904a,b redirect motor rotation of the drive input 1902 to be perpendicular to the shaft 1602 (FIGS. 18A-18B). Through the depicted gear train arrangement, rotation of the drive input 1902 will correspondingly move the rack gears 1808 (FIGS. 18A-18B). In other embodiments, other known gearing mechanisms may be utilized or combined in any number of configurations and dimensioned for optimal torque and/or speed outputs. In at least one embodiment, for example, the gear train may incorporate worm gears or a combination of bevel and spur gears. Moreover, in at least one embodiment, the gear train may be omitted and rotating the drive input 1902 may directly drive an adjacent sliding rack gear 1808 without departing from the scope of the disclosure.

While the spur linkage subassembly 1804 shown in FIG. 19 is described with reference to interfacing with a sliding rack gear 1808 (FIGS. 18A-18B), the foregoing description is equally applicable to a spur linkage subassembly 1804 configured to interface with the shaft rack gear 1812. In such embodiments, the drive input 1902 may be referred to as a "shaft drive input," which may be configured to cause the shaft drive gear 1806a (FIGS. 18A-18B) to rotate (operate) and drive against the shaft rack gear 1812. Driving against the shaft rack gear 1812, as mentioned above, will cause the shaft 1602 (FIGS. 18A-18B) to move (translate) axially relative to (i.e., through) the handle 1612 (FIGS. 18A-18B).

Still referring to FIG. 19, the spur linkage subassembly 1804 may further include a first or "upper" linkage 1910a and a second or "lower" linkage 1910b. As illustrated, one end of the upper linkage 1910a may provide or otherwise define a pair of pins 1912 configured to help pivotably couple the upper linkage 1910a to the upper mounting assembly 1802a (FIGS. 18A-18B). The pins 1912, however, could be replaced with any other type of pivotable coupling engagement mechanism or structure, without departing from the scope of the disclosure. The opposing end of the upper linkage 1910a may be pivotably coupled to one end of the lower linkage 1910b, and the opposing end of the lower linkage 1910b may be rotatably mounted to the axle 1906, which, as mentioned above, can be rotatably mounted to the lower mounting assembly 1802b (FIGS. 18A-18B).

Referring again to FIGS. 18A-18B, with continued reference to FIG. 19, in some embodiments, the spur linkage subassemblies 1804 may be spring biased to the disengaged position, shown in FIG. 18A. In the disengaged position, the drive gears 1806 are disengaged from the sliding rack gears 1808 and the shaft drive gear 1806a is disengaged from the shaft rack gear 1812. The spur linkage subassemblies 1804 are transitioned to the engaged position by collapsing the axial distance between the upper and lower mounting assemblies 1802a,b. As the upper mounting assembly 1802a is lowered toward the lower mounting assembly 1802b, the spur linkage subassemblies 1804 will pivot in tandem at the pivotably coupled linkages 1910a,b toward the engaged (closed) position, as shown in FIG. 18B. In the engaged position, each drive gear 1806, 1806a engages and mates with the adjacent sliding rack gear 1808 or shaft rack gear 1812 simultaneously. Accordingly, the upper linkage 1910a may be configured to move linearly up and down to move the drive gears 1806, 1806a away from and toward the axis of the shaft 1602 as the actuation system 1800 transitions between the open and closed positions.

Figure 20:
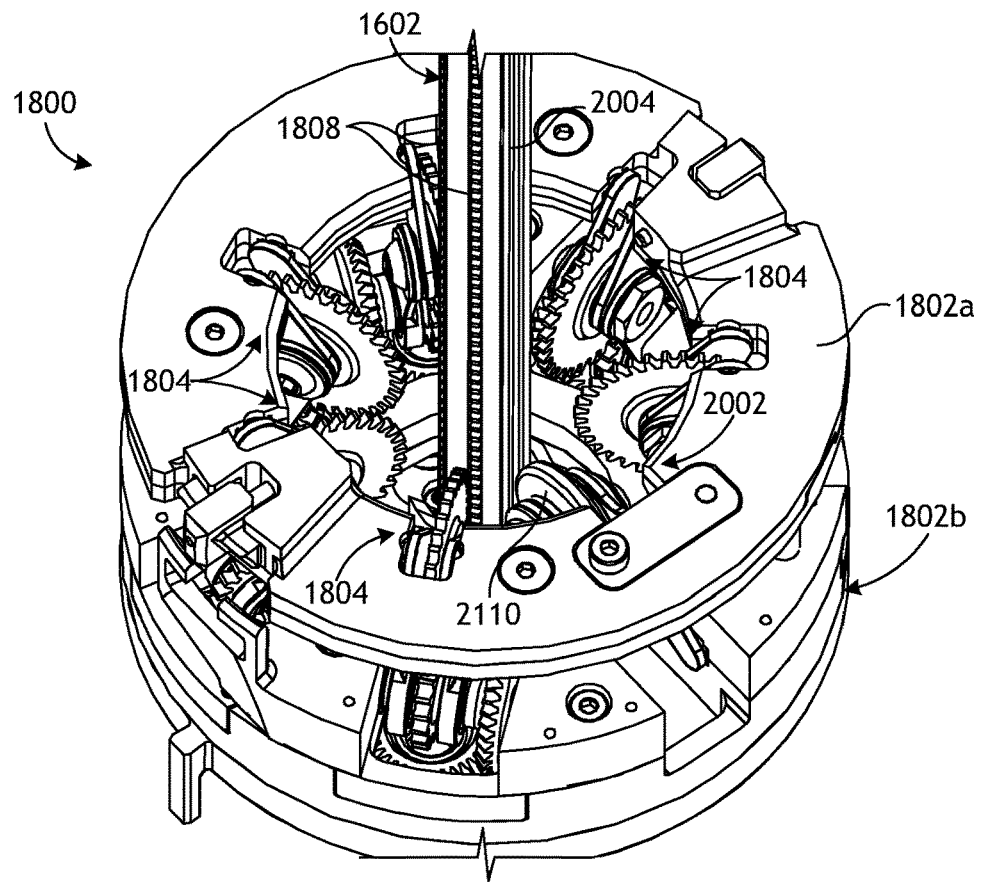
FIG. 20 is another isometric view of the actuation system of FIGS. 18A-18B.

Referring now to FIG. 20, in some embodiments, the actuation system 1800 may further include a clocking wheel linkage subassembly 2002 configured to help properly align (e.g., angularly, rotationally, etc.) the actuation system 1800 with the shaft 1602.

Figure 21:
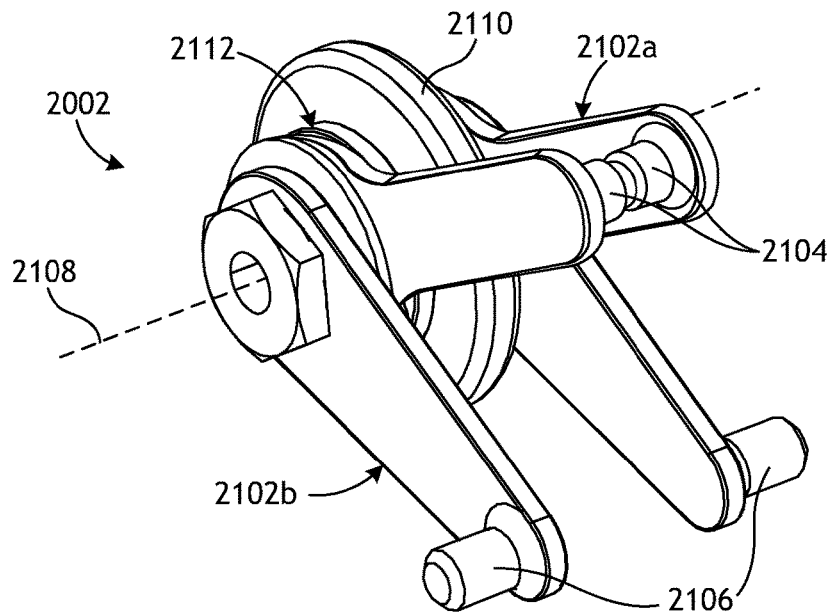
FIG. 21 is an enlarged, isometric view of one example of the clocking wheel linkage subassembly, according to one or more embodiments.

FIG. 21 is an enlarged, isometric view of one example of the clocking wheel linkage subassembly 2002, according to one or more embodiments. As illustrated, the clocking wheel linkage subassembly 2002 may include a first or "upper" linkage 2102a and a second or "lower" linkage 2102b. One end of the upper linkage 2102a may provide or otherwise define a pair of pins 2104 configured to help pivotably couple the upper linkage 2102a to the upper mounting assembly 1802a (FIG. 20). Similarly, one end of the lower linkage 2102b may also provide or otherwise define a pair of pins 2106 configured to help pivotably couple the lower linkage 2102a to the lower mounting assembly 1802b. The pins 2104, 2106, however, could be replaced with any other type of pivotable coupling engagement mechanism or structure, without departing from the scope of the disclosure. The opposite ends of the linkages 2102a,b may be pivotably attached to each other at a pivot axis 2108.

The clocking wheel linkage subassembly 2002 may also include a clocking wheel 2110 rotatably mounted at the pivot axis 2108. In some embodiments, one or more thrust bearings and/or washers 2112 (e.g., belleville washers) may help maintain the pivotably mounted linkages 2102a,b and clocking wheel 2110 axially tight and rotationally free at the pivot axis 2108.

Referring again to FIG. 20, with continued reference to FIG. 21, similar to the spur linkage subassemblies 1804, the clocking wheel linkage subassembly 2002 may be pivotably mounted to the mounting assemblies 1802a,b and configured to pivot between a first or "disengaged" position, as shown in FIG. 18A, and a second or "engaged" position, as shown in FIGS. 18B and 20. Upon transitioning to the engaged position, the clocking wheel 2110 may be received within and otherwise mate with a longitudinal groove 2004 defined along all or a portion of the shaft 1602. Receiving the clocking wheel 2110 within the groove 2004 will help properly align all the spur linkage subassemblies 1804 rotationally (angularly) with the proper sliding rack gears 1808 or shaft rack gear 1812 (FIGS. 18A-18B).

Figure 22A:
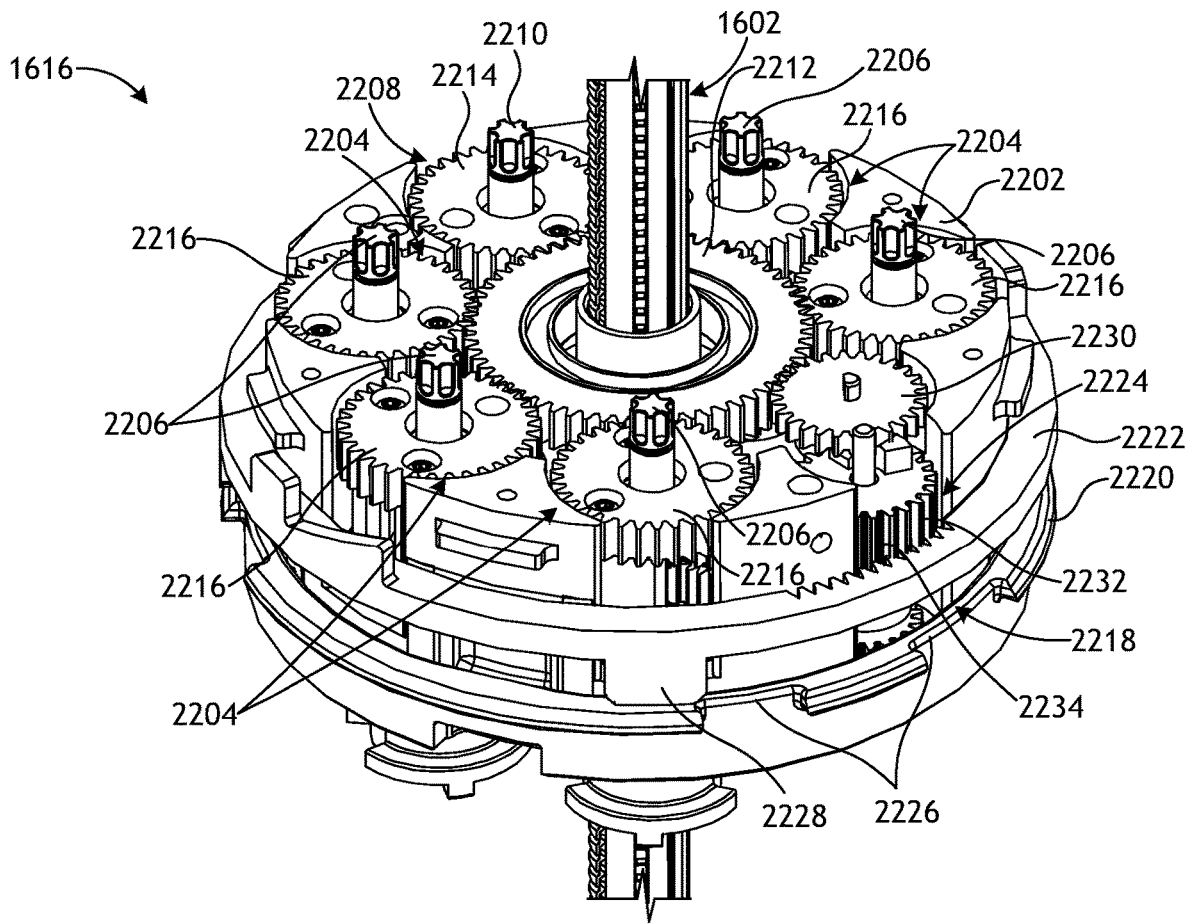
FIGS. 22A and 22B are isometric top and bottom views, respectively, of one example of the decoupler of FIG. 16, according to one or more embodiments.
Figure 22B:
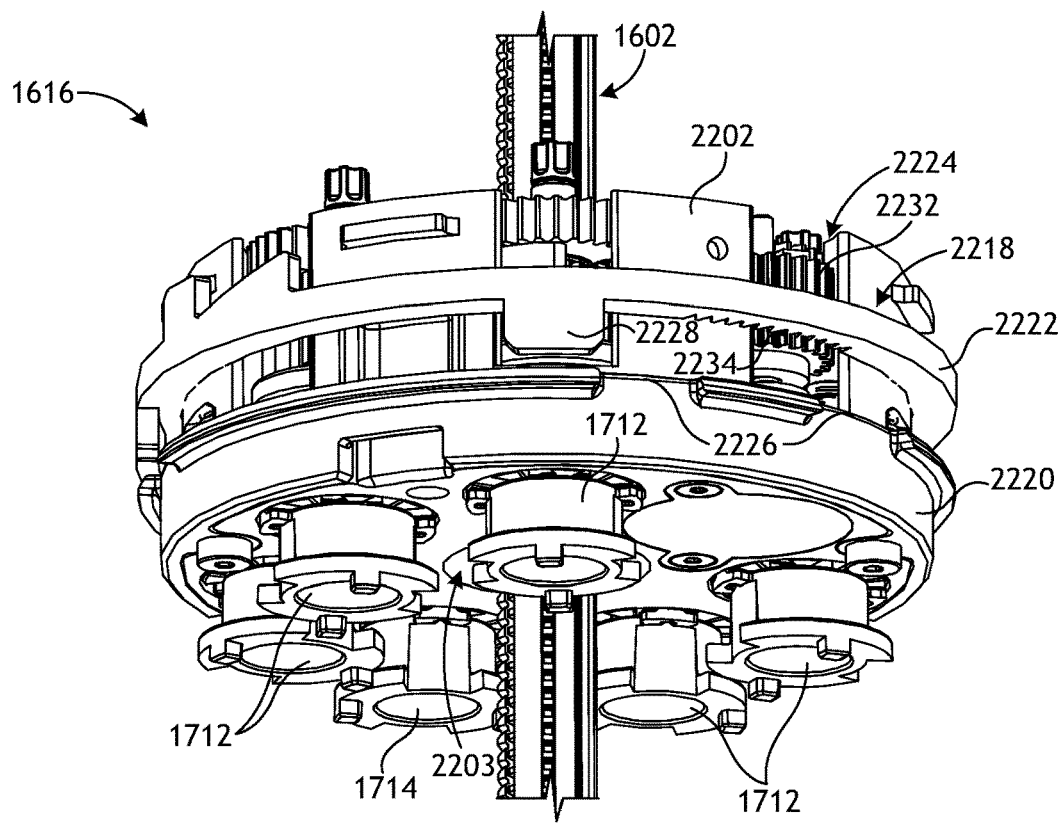

FIGS. 22A and 22B are isometric top and bottom views, respectively, of one example of the decoupler 1616 of FIG. 16, according to one or more embodiments. As discussed above, the decoupler 1616 may interpose the handle 1612 (FIGS. 16-17) and the instrument driver 1614 (FIGS. 16-17), and may otherwise operate to transfer torque from the drive outputs 1710 (FIG. 17) of the instrument driver 1614 to the drive inputs of the handle 1612. The architecture of the decoupler 1616 further allows for the transfer of insertion motion (e.g., movement of the shaft 1602) to all the drive inputs of the handle 1612, thus allowing one robot motor from the instrument driver 1614 to control insertion of the surgical tool 1600, while allowing the other driver motors to drive the sliding rack gears independent of insertion.

The decoupler 1616 may include a generally circular housing 2202 that defines a central aperture 2203 (FIG. 22B), and the shaft 1602 may extend concentrically through the housing 2202 via the central aperture 2203. As best seen in FIG. 22A, a plurality of differential assemblies 2204 may be rotatably mounted to the housing 2202. As seen in FIG. 22B, each differential assembly 2204 can include a corresponding one of the differential inputs 1712, which, as described above, are matable with corresponding drive outputs 1710 (FIG. 17) of the instrument driver 1614 (FIGS. 16-17). Consequently, each motor in the instrument driver 1614 drives a corresponding differential assembly 2104. Once properly mated (coupled) with a corresponding drive output 1710, each differential input 1712 will share an axis of rotation with the corresponding drive output 1710 of the instrument driver 1614 to allow the transfer of rotational torque from the drive output 1710 to the corresponding differential input 1712.

As best seen in FIG. 22A, each differential assembly 2204 may also include a differential output 2206, which can be operatively coupled to a corresponding drive input 1902 (FIG. 19) of the actuation system 1800 (FIGS. 18A-18B). In some embodiments, one or more intermediate structures, gearing, or mechanisms may interpose the differential output 2206 and an adjacent drive input 1902. Once properly coupled, however, the drive input 1902 will share an axis of rotation with the corresponding differential output 2206 to allow rotational torque from the differential output 2206 to be transferred to the corresponding drive input 1902. Accordingly, once the decoupler 1616 is properly installed between the handle 1612 (FIG. 16) and the instrument driver 1614 (FIG. 16), the drive inputs 1902 will share axes of rotation with the corresponding drive outputs 1710 of the instrument driver 1614 (FIG. 16) via the decoupler 1616, which allows the transfer of rotational torque from the drive outputs 1710 to the corresponding drive inputs 1902.

The decoupler 1616 further includes an insertion assembly 2208 also rotatably mounted to the housing 2202. As seen in FIG. 22B, the insertion assembly 2208 includes the insertion input 1714 described above, which is matable with a corresponding one of the drive outputs 1710 (FIG. 17) of the instrument driver 1614 (FIGS. 16-17); referred to herein as a "shaft drive output". Once the insertion input 1714 is properly mated with the corresponding shaft drive output 1710, the insertion input 1714 will share an axis of rotation with the shaft drive output 1710 to allow the transfer of rotational torque from the shaft drive output 1710 to the insertion input 1714.

As seen in FIG. 22A, the insertion assembly 2208 further includes an insertion output 2210, which can be operatively coupled to a corresponding drive input 1902 (FIG. 19) of the actuation system 1800 (FIGS. 18A-18B); referred to herein as the "shaft drive input". In some embodiments, one or more intermediate structures, gearing, or mechanisms may interpose the insertion output 2210 and the shaft drive input 1902. Once properly coupled, however, the insertion output 2210 will share an axis of rotation with the shaft drive input 1902 to allow the transfer of rotational torque from the insertion output 2210 to the corresponding shaft drive input 1902. Accordingly, once the decoupler 1616 is properly installed between the handle 1612 (FIG. 16) and the instrument driver 1614 (FIG. 16), the shaft drive input 1902 will share an axis of rotation with the shaft drive output 1710 (FIG. 17) of the instrument driver 1614 (FIG. 16) via the decoupler 1616, which allows the transfer of rotational torque from the shaft drive output 1710 to the shaft drive input 1902.

In the case of an insertion-coupled instrument, such as the surgical tool 1600 (FIG. 16), when the shaft 1602 is inserted or retracted, all the sliding rack gears 1808 (FIGS. 18A-18B) need to move at the same rate to maintain the position of the wrist 1606 (FIG. 16). One solution to accomplish this may be to have all the motors of the instrument driver 1614 (FIGS. 16-17) jointly perform the coupled motion. In this solution, however, the power requirements for the motors increases because the performance of the surgical tool 1600 is based on maintaining a grip force and a tip velocity. If the motors were to drive in a coupled fashion, then the motors would have to move faster and still maintain the same force output. This is particularly difficult because the required insertion velocity is much higher than the velocity to drive the sliding rack gears 1808.

In contrast, the decoupler 1616 allows the surgical tool 1600 (FIG. 1) with coupled motions to be driven by uncoupled inputs. More specifically, the decoupler 1616 allows one motor from the instrument driver 1614 (FIG. 16) to control insertion of the surgical tool 1600 (i.e., axial movement of the shaft 1602 of FIG. 16) while simultaneously allowing the other motors of the instrument driver 1614 to drive the sliding rack gears 1808 (FIGS. 17A-17B and 18A-18D) independent of insertion. To accomplish this, the decoupler 1616 includes a differential gear train, which can include a system of mechanically-linked differential subassemblies that allow the insertion input 1714 to simultaneously drive each differential output 2206 of the decoupler 1616, while also allowing each differential input 1712 to independently drive the corresponding differential output 2206.

As best seen in FIG. 22A, the differential gear train includes an insertion transmission gear 2212 that may be driven by an insertion input gear 2214 mounted to and otherwise forming part of the insertion assembly 2208. As the insertion assembly 2208 is driven (rotated), the insertion input gear 2214 drives against and causes the insertion transmission gear 2212 to rotate, and the insertion transmission gear 2212 is arranged to interface with a differential insertion input gear 2216 mounted to and otherwise forming part of each differential assembly 2204. As the insertion transmission gear 2212 drives against the differential insertion input gears 2216 simultaneously, each differential assembly 2204 correspondingly rotates.

Accordingly, the insertion assembly 2208 is coupled to all the differential assemblies 2204 in the decoupler 1616 by a single gear; i.e., the insertion transmission gear 2212. Thus, when insertion is driven by operation (rotation) of the insertion assembly 2208, each of the differential assemblies 2204 is simultaneously rotated, which means that by driving the insertion input 1714, all the differential outputs 2206 simultaneously rotate. Additionally, if a motor input to any of the differential assemblies 2204 is rotated, then the corresponding differential output 2206 is simultaneously rotated. As will be appreciated, the result of this is the separation of the insertion motion from the motions (articulation) of the wrist 1606 (FIG. 16).

Dwell Slip Clutch Insertion Lockout

In many articulable surgical tools, such as the surgical tool 1600 of FIG. 16, an insertion lockout safety feature is incorporated to prevent an operator from removing the surgical tool 1600 from the instrument driver 1614 (FIGS. 16-17) when the shaft 1602 (FIGS. 16-17) is not in the fully retracted position. This safety feature not only reduces the likelihood of incorrect installation in future cases or attachments, but also prevents an operator from inadvertently detaching the surgical tool 1600 when the end effector 1604 (FIGS. 16-17) remains located inside a patient's body.

Some surgical tool insertion lockout mechanisms include a ring gear or "lockout ring" that is mechanically linked to the insertion input such that when the insertion input is actuated, it rotates the lockout ring. The lockout ring is keyed around its outer diameter to interface with a latching mechanism, and when the lockout ring is not in a predetermined "home" position, the latching ring cannot be manipulated to remove the tool from the instrument driver. In prior configurations, the lockout ring is constantly driven during all phases of device insertion, which adds unnecessary parasitic drag forces to the system.

According to embodiments of the present disclosure, the surgical tool 1600 (FIGS. 16-17) may include an insertion lockout mechanism designed rotate the lockout ring only a small amount during device insertion, and thus eliminating the constant travel of the lockout ring during operation. As described herein, the insertion lockout mechanism may include a dwell slip clutch designed interface with the lockout ring. The dwell slip clutch may be configured to move (rotate) the lockout ring only a small amount on initial insertion, and then remain motionless (e.g., "dwell") for the remainder of the insertion stroke. This may prove advantageous in reducing parasitic drag forces of the lockout ring during device insertion.

Still referring to FIGS. 22A-22B, an example insertion lockout mechanism 2218 may also be included in the decoupler 1616, in accordance with one or more embodiments of the disclosure. While the insertion lockout mechanism 2218 is shown and described herein as forming part of the decoupler 1616, the insertion lockout mechanism 2218 could alternatively form part of another portion of the surgical tool 1616 (FIGS. 16-17), without departing from the scope of the disclosure.

As illustrated the insertion lockout mechanism 2218 may include a latch ring 2220, a lockout ring 2222, and a dwell slip clutch 2224. The latch ring 2220 and the lockout ring 2222 may each extend about (i.e., circumscribe) the outer diameter of the housing 2202, and may be vertically (e.g., axially) offset from each other along a central axis of the decoupler 1616. The latch ring 2220 may define one or more grooves or slots 2226 and the lockout ring 2222 may define a corresponding one or more tabs 2228 configured to be received within (e.g. mate with) the one or more slots 2226 when the lockout ring 2222 is rotated to angularly align the tabs 2228 and the slots 2226. In other embodiments, the latch ring 2220 may define the tabs 2228 and the lockout ring 2222 may define the slots 2226, or alternatively the latch ring 2220 and the lockout ring 2222 may each provide a combination of slots 2226 and tabs 2228, without departing from the scope of the disclosure.

The latch ring 2220 may be compliantly mounted (e.g., spring-biased) to the housing 2202 and naturally biased away from the lockout ring 2222. The latch ring 2220 may be movable between a first or "locked" position, where the latch ring 2220 and the lockout ring 2222 are vertically (axially) offset from each other and the tabs 2228 and the slots 2226 are otherwise not aligned or mated, and a second or "unlocked" position, where the tabs 2228 and the slots 2226 are angularly aligned and the latch ring 2220 is moved axially toward the lockout ring 2222 to mate the tabs 2228 with the slots 2226. The latch ring 2220 is shown in FIGS. 22A-22B in the "locked" position. Transitioning the lockout ring 2222 to the unlocked position allows the handle 1612 (FIGS. 16-17) to be detached (separated) from the instrument driver 1614 (FIGS. 16-17). In some embodiments, moving the latch ring 2220 to the unlocked position may be done manually. In such embodiments, an operator (e.g., a nurse, a practitioner, a user, etc.) may manually grasp a portion of the latch ring 2220 or the handle 1612 and force the latch ring 2220 axially toward the lockout ring 2222. In other embodiments, however, the latch ring 2220 may be mechanically moved to the unlocked position, such as through an automated system or the like.

The dwell slip clutch 2224 may be operable to rotate the lockout ring 2222 relative to the housing 2202 and thereby angularly align or misalign the tabs 2228 with the slots 2226. Accordingly, the dwell slip clutch 2224 may be configured to transition the lockout ring 2222 between a "misaligned" position, where the tabs 2228 are misaligned with the slots 2226 and the latch ring 2220 is thereby prevented from moving to the unlocked position, and an "aligned" position, where the tabs 2228 are aligned with the slots 2226, thus allowing the latch ring 2220 to move to the unlocked position.

Operation (actuation) of the dwell slip clutch 2224 may be driven by device insertion. More particularly, actuating the insertion assembly 2208 will cause the insertion transmission gear 2212 to rotate, and rotation of the insertion transmission gear 2212 may cause the dwell slip clutch 2224 to operate. As illustrated, the dwell slip clutch 2224 may include a driven gear 2230 and an output clutch gear 2232. The driven gear 2230 may be arranged to interface with the insertion transmission gear 2212 such that rotation of the insertion transmission gear 2212 rotates the driven gear 2230, and rotating the driven gear 2230 can cause the output clutch gear 2232 to rotate, as discussed below.

The output clutch gear 2232 may be arranged to interface with and drive the lockout ring 2222. As illustrated, a sector gear 2234 may be provided (defined) on a portion of the inner diameter of the lockout ring 2222, and rotating the output clutch gear 2232 may engage and drive the sector gear 2234 to thereby rotate the lockout ring 2222 relative to the housing 2202. In some embodiments, the sector gear 2234 may have an arc length of about 15°, but could alternatively have an arc length greater or less than 15° without departing from the scope of the disclosure. As the output clutch gear 2232 rotates, it correspondingly drives the lockout ring 2222 a small amount of rotation to angularly align the tabs 2228 with the slots 2226, thus enabling the latch ring 2220 to be moved axially to the unlocked position.

When the insertion assembly 2208 is operated to cause the shaft 1602 to advance distally, the output clutch gear 2232 drives the lockout ring 2222 to angularly misalign the tabs 2228 and the slots 2226. This prevents the lockout ring 2222 from moving to the unlocked position and inadvertently detaching the handle 1612 (FIGS. 16-17) from the instrument driver 1614 (FIGS. 16-17) with the shaft 1602 extended. As discussed below, rotating the dwell slip clutch 2224 a predetermined angular distance (amount) in a first angular direction (e.g., clockwise) can disengage the output clutch gear 2232 such that the output clutch gear 2232 is no longer able to drive the lockout ring 2222 during device insertion. This eliminates any additional parasitic drag that the lockout ring 2222 would add to the system during normal insertion of the device. Upon rotating the dwell slip clutch 2224 in a second angular direction (e.g., counter-clockwise), the output clutch gear 2232 will eventually become reengaged and able to drive the lockout ring 2222 in the opposite direction.

Figure 23:
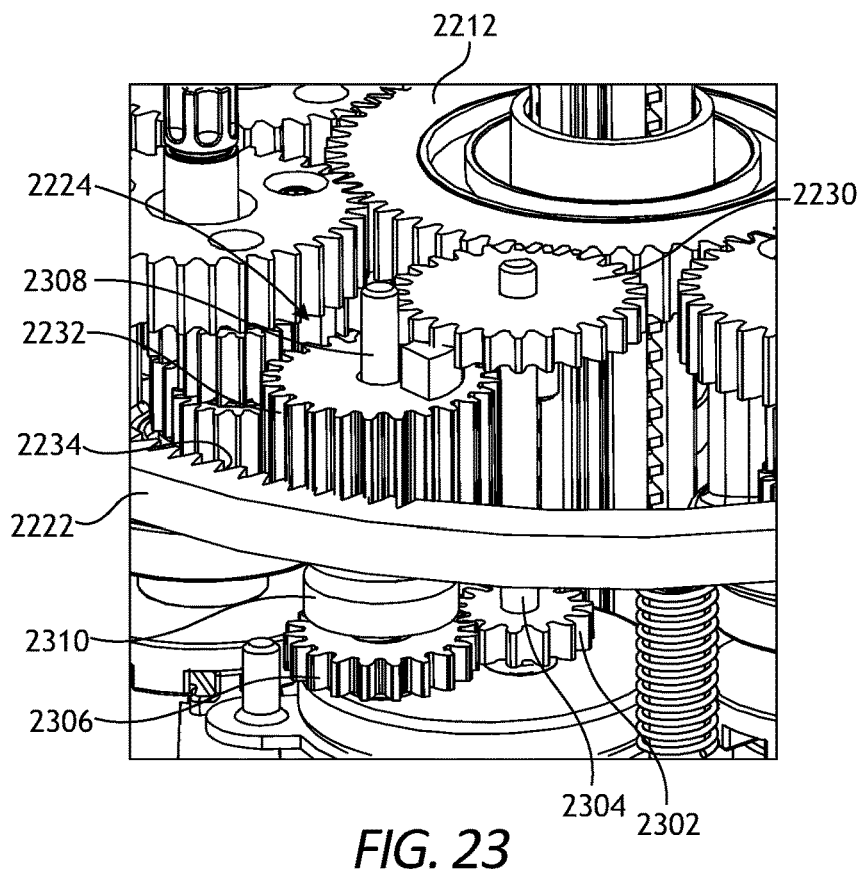
FIG. 23 is an enlarged side view of the dwell slip clutch, according to one or more embodiments.

FIG. 23 is an enlarged side view of the dwell slip clutch 2224 mounted within the housing 2202, according to one or more embodiments. While the dwell slip clutch 2224 is described and depicted herein in a particular configuration and design, those skilled in the art will readily appreciate that the dwell slip clutch 2224 may exhibit other alternative configurations or designs and still perform the same function, without departing from the scope of the disclosure. As mentioned above, the driven gear 2230 may be arranged to interface with and otherwise be driven by the insertion transmission gear 2212. The driven gear 2230 may be operatively coupled to a pinion gear 2302 via a common axle 2304, such that rotating the driven gear 2230 correspondingly rotates the axle 2304 and the pinion gear 2302.

In some embodiments, the pinion gear 2302 can be dimensioned relative to the co-axially aligned driven gear 2230 such that motion of the insertion transmission gear 2212 may be scaled to achieve a targeted input of the dwell slip clutch 2224. In other embodiments, however, the pinion gear 2302 may be dimensioned such that no motion scaling is achieved. In yet other embodiments, the driven gear 2230 and the pinion gear 2302 may be omitted from the system, and the insertion transmission gear 2212 may be arranged to directly drive the output clutch gear 2232, without departing from the scope of the disclosure.

The pinion gear 2302 may be arranged to interface with an input clutch gear 2306 rotatably mounted to a common axle 2308. The output clutch gear 2232 is also rotatably mounted to the common axle 2308, and one or more dwell disks 2310 (one shown) may axially interpose the output and input clutch gears 2232, 2306. While only one dwell disk 2310 is shown in FIG. 23, more than one may be included. The dwell slip clutch 2224 may be movable between a first or "collapsed" state and a second or "expanded" state. When the dwell slip clutch 2224 is in the collapsed state, the output and input clutch gears 2232, 2306 and the dwell disk 2310 are axially collapsed toward each other such that any rotation of the input clutch gear 2306 correspondingly drives rotation of the dwell disk 2310 and the output clutch gear 2232, thus creating direct input-output motion. Moreover, in the collapsed state, the output clutch gear 2232 rotates and drives against the sector gear 2234 defined on the lockout ring 2222. In contrast, when the dwell slip clutch 2224 is transitioned to the expanded state, the output and input clutch gears 2232, 2306 and the dwell disk 2310 are axially separated and allowed to rotate independent of each other, such that rotating the input clutch gear 2232 does not directly drive rotation of the output clutch gear 2232.

Figure 24A:
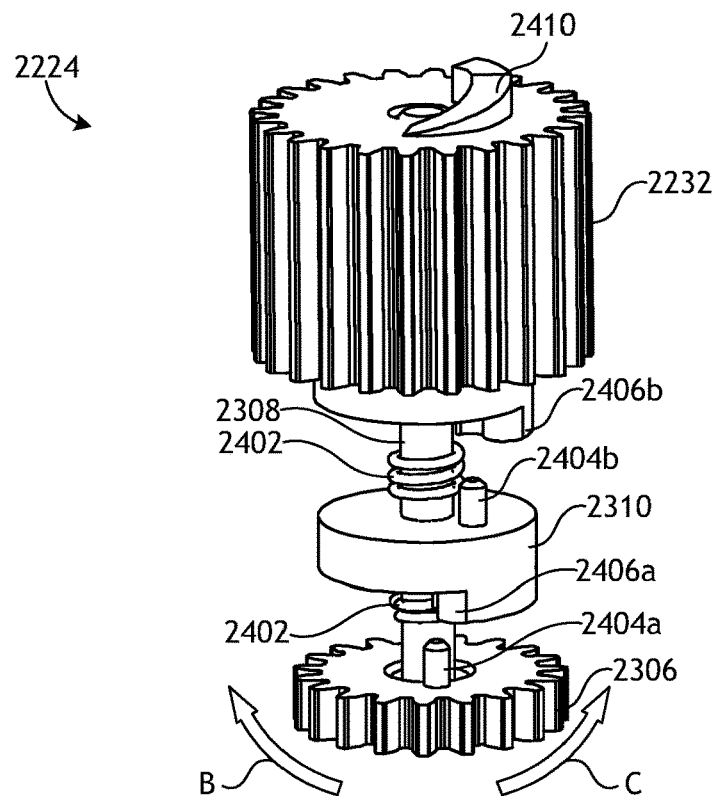
FIGS. 24A and 24B are partially exploded, isometric top and bottom views, respectively, of the dwell slip clutch.
Figure 24B:
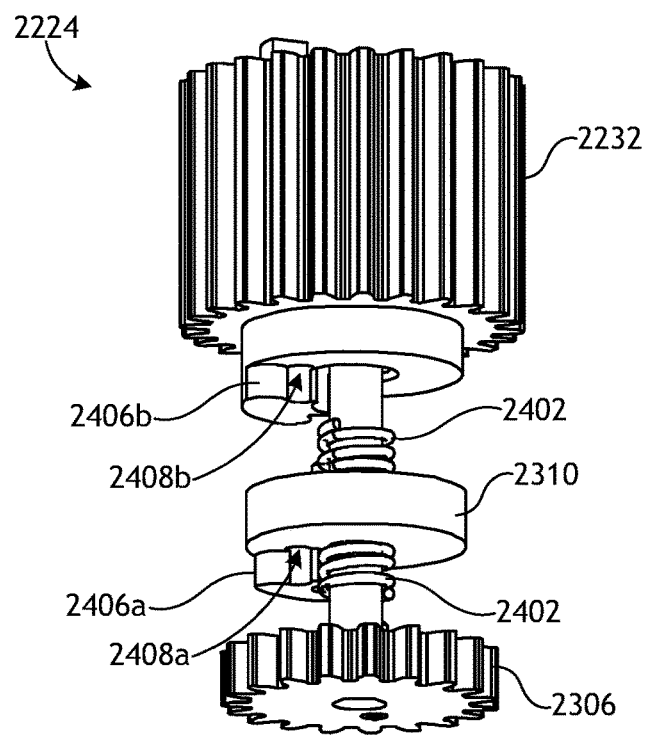

FIGS. 24A and 24B are partially exploded, isometric top and bottom views, respectively, of the dwell slip clutch 2224, according to one or more embodiments. As shown, the input clutch gear 2306, the dwell disk 2310, and the output clutch gear 2232 are rotatably mounted to the common axle 2308. One or more springs 2402 may be arranged between the input clutch gear 2306 and the dwell disk 2310, and also between the dwell disk 2310 and the output clutch gear 2232. The springs 2402 may be configured to naturally bias the dwell slip clutch 2224 to the expanded state by passively biasing the input clutch gear 2306 away from the dwell disk 2310, and passively biasing the output clutch gear 2232 away from the dwell disk 2310.

A first axial drive pin 2404a may be defined on the upper surface of the input clutch gear 2306 and configured to laterally engage a first raised shoulder 2406a defined on an opposing bottom surface of the dwell disk 2310. A second axial drive pin 2404b may be defined on the upper surface of the dwell disk 2310 and configured to laterally engage a second raised shoulder 2406b defined on an opposing bottom surface of the output clutch gear 2232. The axial drive pins 2404a,b may each be offset from (eccentric to) the common axle 2308. When the dwell slip clutch 2224 is in the expanded state, the first and second axial drive pins 2404a,b are able move relative to the adjacent first and second raised shoulders 2406a,b. Upon the first axial drive pin 2404a engaging one side (e.g., an end wall) of the first raised shoulder 2406a, further movement of the first axial drive pin 2404a in the same angular direction will force the dwell disk 2310 to rotate in the same direction. Similarly, once the second axial drive pin 2404b engages one side (e.g., an end wall) of the second raised shoulder 2406b, any further movement of the second axial drive pin 2404b in the same angular direction will force the output clutch gear 2232 to rotate in the same direction.

As best seen in FIG. 24B, a first pocket 2408a may be defined in the bottom surface of the dwell disk 2310 adjacent the first raised shoulder 2406a, and a second pocket 2408b may be defined in the bottom surface of the output clutch gear 2232 adjacent the second raised shoulder 2406b. When the dwell slip clutch 2224 is moved to the collapsed state, the first axial drive pin 2404a may be received within the first pocket 2408a, and the second axial drive pin 2404b may be received within the second pocket 2408b. With the axial drive pins 2404a,b received within the pockets 2408a,b, this allows the entire dwell slip clutch 2224 to rotate in unison as the input clutch gear 2306 is rotated. In other words, when the axial drive pins 2404a,b are received within the pockets 2408a,b, the stacked gears are rotationally keyed together with no dwell, thus creating direct input-output motion.

As best seen in FIG. 24A, a ramp 2410 may be defined on the top of the output clutch gear 2232. When the dwell slip clutch 2224 is properly mounted within the housing 2202 (FIG. 22A), the ramp 2410 may be arranged to engage and otherwise interact with an opposing ramp provided on a top housing and arranged vertically above the ramp 2410.

Figure 25A:
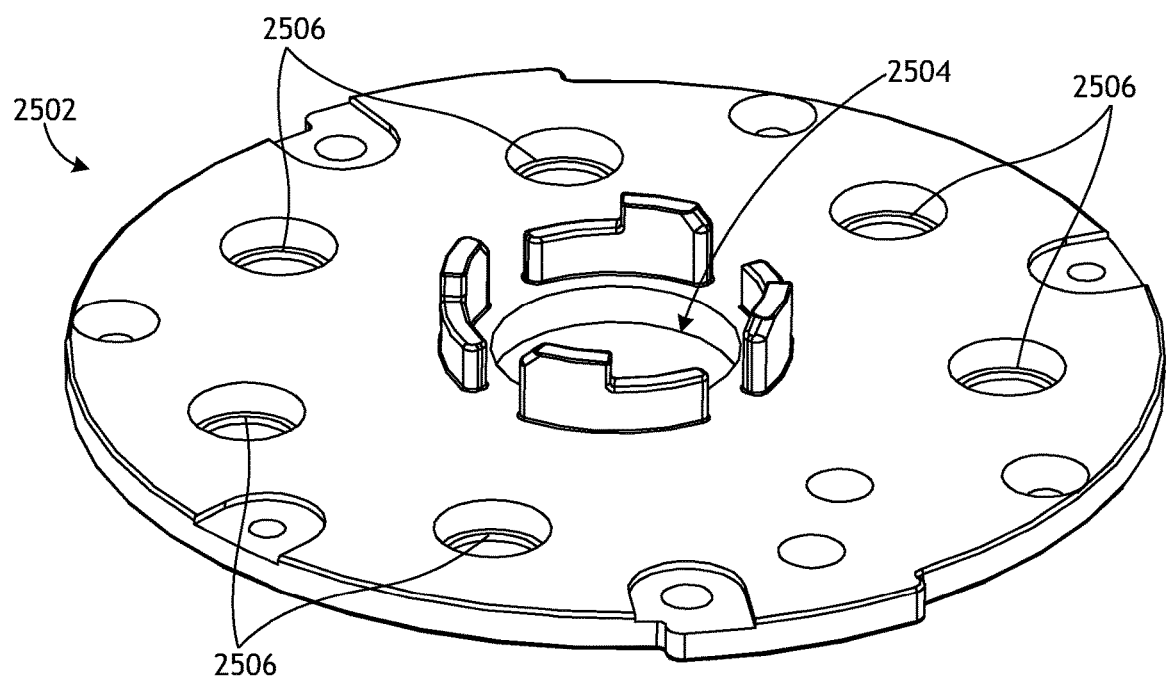
FIGS. 25A and 25B illustrate an example top housing.
Figure 25B:
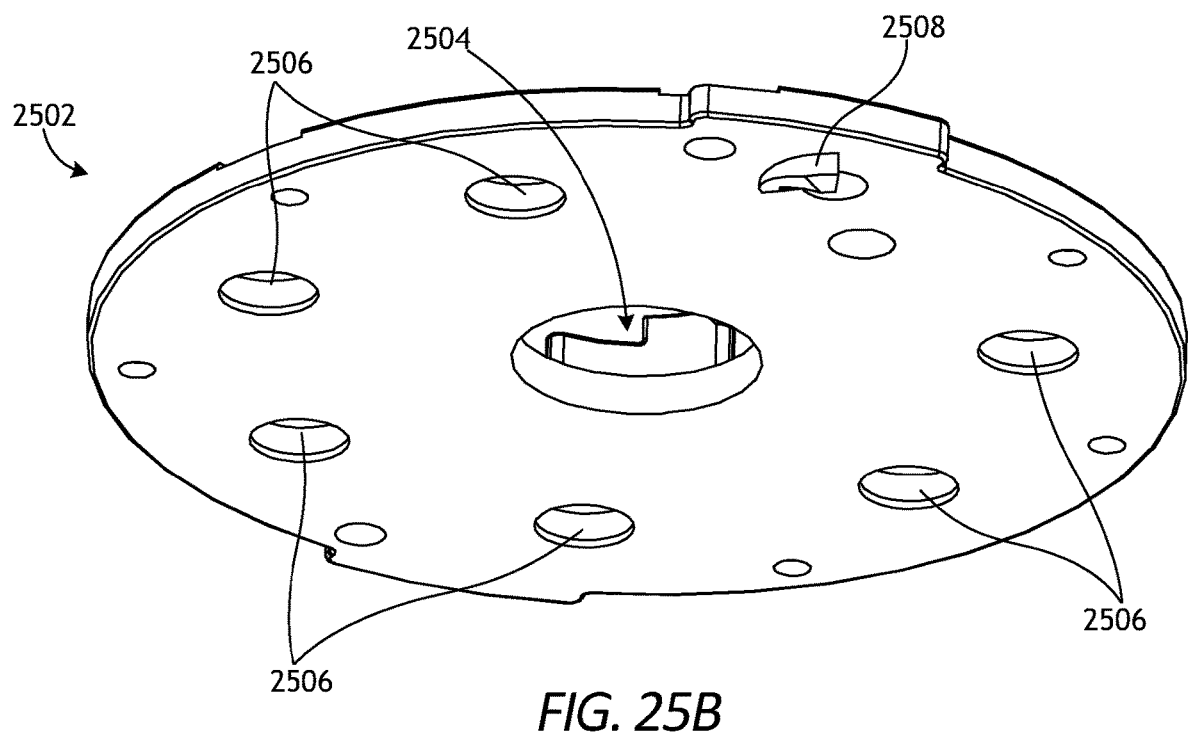

Referring briefly to FIGS. 25A and 25B, illustrated is an example top housing 2502, alternately referred to as a "housing plate," that may be mounted to the top of the housing 2202 (FIGS. 22A-22B). The top housing 2502 may be configured to secure the differential assemblies 2204 (FIG. 22A), the insertion assembly 2208 (FIG. 22A), and the dwell slip clutch 2224 (FIGS. 22A-22B, 23, 24A-25B) within the housing 2202. As illustrated, the top housing 2502 defines a central aperture 2504 through which the shaft 1602

(FIGS. 22A-22B) can extend. The top housing 2502 also defines a plurality of apertures 2506 configured to receive the differential outputs 2206 (FIG. 22A) of each differential assembly 2204 and the insertion output 2210 (FIG. 22A) of the insertion assembly 2208. As seen in FIG. 25B, the top housing 2502 may also define an opposing ramp 2508 arranged to engage and otherwise interact with the ramp 2410 (FIG. 24A) provided on the top of the output clutch gear 2232 (FIG. 24A) when the top housing 2502 is properly mounted to the housing 2202.

Referring again to FIGS. 24A-24B, with continued reference to FIGS. 25A-25B, example operation of the dwell slip clutch 2224 is now provided. With the dwell slip clutch 2224 in the expanded state, the input clutch gear 2306 may be rotated in a first angular direction B (FIG. 24A) until the first axial drive pin 2404a locates one side of the first raised shoulder 2406a, at which point the dwell disk 2310 will also be forced to rotate in the first angular direction B. The input clutch gear 2306 and the dwell disk 2310 may then jointly rotate in the first angular direction B until the second axial drive pin 2404b locates one side of the second raised shoulder 2406b, at which point the output clutch gear 2232 will also be rotated in the first angular direction B. The time required for the axial drive pins 2404a to rotate and locate the raised shoulders 2406a,b is referred to herein as "dwell" or "dwell time".

With the axial drive pins 2404a,b laterally engaged against the raised shoulders 2406a,b and also axially aligned with the pockets 2408a,b, the dwell slip clutch 2224 is poised to be transitioned from the expanded state to the collapsed state. Rotating the output clutch gear 2232 further in the first angular direction B will drive the opposing ramps 2410, 2508 against each other, and such relative sliding engagement between the ramps 2410, 2508 forces the output clutch gear 2232 downward and drives the axial drive pins 2404a,b into the pockets 2408a,b. Forcing the output clutch gear 2232 downward also compresses the springs 2402 and forces the dwell disk 2310 against the input clutch gear 2306 as the dwell slip clutch 2224 transitions to the collapsed state. In the collapsed state, the stacked gears are rotationally keyed together with no dwell, thus creating direct input-output motion. Moreover, in the collapsed state, the output clutch gear 2232 can drive the lockout ring 2222 (FIGS. 22A-22B, 23), as discussed herein.

To transition the dwell slip clutch 2224 back to the expanded state, the input clutch gear 2306 may be rotated in a second angular direction C, opposite the first angular direction B. This will cause the output clutch gear 2232 to also be rotated in the second angular direction C until the opposing ramps 2410, 2508 become disengaged, at which point the built-up spring force of the springs 2402 will urge the input clutch gear 2306 away from the dwell disk 2310, and simultaneously urge the output clutch gear 2232 away from the dwell disk 2310. In this process, the axial drive pins 2404a,b will also be disengaged from the pockets 2408a,b. In the expanded state, rotating the input clutch gear 2306 (via the pinion gear 2302 of FIG. 23) does not act on the dwell disk 2310 and, therefore, cannot cause the output clutch gear 2232 to rotate and drive the lockout ring 2222, which ensures that no additional parasitic drag is added to the system during normal insertion of the device.

With the dwell slip clutch 2224 in the expanded state, the input clutch gear 2306 may be continually rotated in the second angular direction C until the first axial drive pin 2404a locates a second or opposite side of the first raised shoulder 2406a, at which point the dwell disk 2310 will also be forced to rotate in the second angular direction C. The input clutch gear 2306 and the dwell disk 2310 may then jointly rotate in the second angular direction C until the second axial drive pin 2404b locates a second or opposite side of the second raised shoulder 2406b, at which point the output clutch gear 2232 will also be rotated in the second angular direction C. Further rotation of the output clutch gear 2232 in the second angular direction C will drive the lockout ring 2222 to angularly align the tabs 2228 (FIGS. 24A-24B) with the slots 2226 (FIGS. 24A-24B) provided on the latch ring 2220, which allows the latch ring 2220 to be transitioned from the locked position to the unlocked position.

Figure 26:
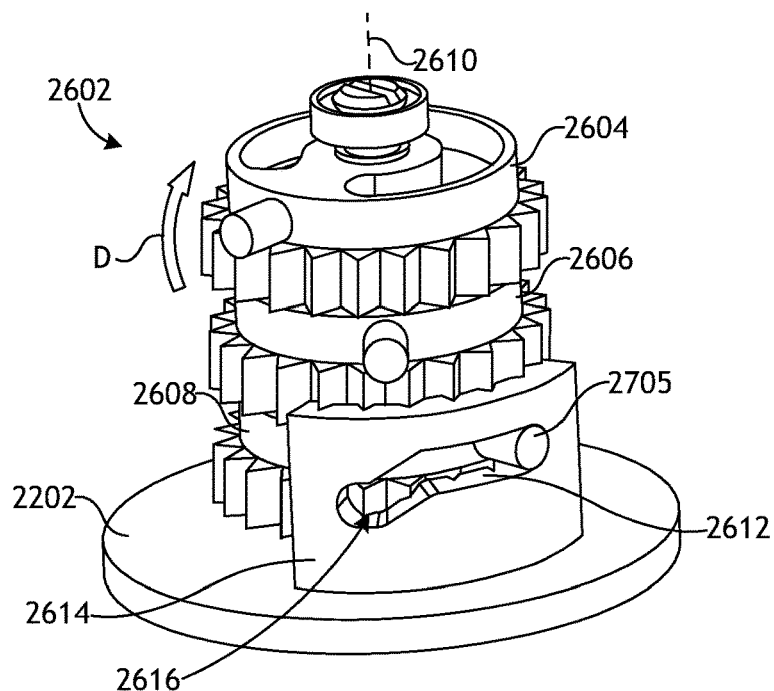
FIG. 26 is an isometric side view of another example dwell slip clutch, according to one or more additional embodiments.

FIG. 26 is an isometric side view of another example dwell slip clutch 2602, according to one or more additional embodiments. The dwell slip clutch 2602 may be similar in some respects to the dwell slip clutch 2224 of FIGS. 22A-22B, 23, 24A-24B, and therefore may be best understood with reference thereto. Similar to the dwell slip clutch 2224, for example, the dwell slip clutch 2602 may be rotatably mounted to the housing 2202 (only a small portion shown in FIG. 26) and operable to rotate the lockout ring 2222 (FIG. 22A-22B) relative to the housing 2202 to thereby angularly align or misalign the tabs 2228 (FIG. 22A-22B) with the slots 2226 (FIG. 22A-22B). Moreover, operation (actuation) of the dwell slip clutch 2602 may be driven by device insertion and, more particularly, by actuating the insertion assembly 2208 (FIG. 22A-22B).

As illustrated, the dwell slip clutch 2602 may include an input clutch gear 2604, a dwell disk 2606, and an output clutch gear 2608. In some embodiments, the input clutch gear 2604 may be arranged to interface directly with the insertion transmission gear 2212 (FIG. 22A-22B) such that rotation of the insertion transmission gear 2212 acts directly on the input clutch gear 2604 and thereby causes the dwell slip clutch 2602 to operate (rotate). In other embodiments, however, the input clutch gear 2604 may be arranged to be driven by other gears, such as the pinion gear 2302 (FIG. 23) and the driven gear 2230 (FIG. 22A-22B), as generally described above. In either scenario, however, rotation of the insertion transmission gear 2212 will ultimately dictate or cause operation (rotation) of the dwell slip clutch 2602.

The dwell disk 2606 axially interposes the input and output clutch gears 2604, 2608. While only one dwell disk 2606 is shown in FIG. 26, more than one may be included in the dwell slip clutch 2602. The output clutch gear 2608 may be arranged to interface with and drive the lockout ring 2222 (FIG. 22A-22B), as generally described above.

In the illustrated embodiment, the input and output clutch gears 2604, 2608 and the dwell disk 2606 comprise stacked gears aligned along a common axis 2610. While FIG. 26 shows the input clutch gear 2604 stacked atop the dwell disk 2606, and the dwell disk 2606 stacked atop the output clutch gear 2608, the position of the input and output clutch gears 2604, 2608 along the common axis 2610 may be switched (reversed), without departing from the scope of the disclosure. Moreover, the design of each of the input and output clutch gears 2604, 2608 and the dwell disk 2606 may be the same, which may prove advantageous in reducing manufacturing costs by requiring only one design for a dwell slip clutch structural component.

Figure 27A:
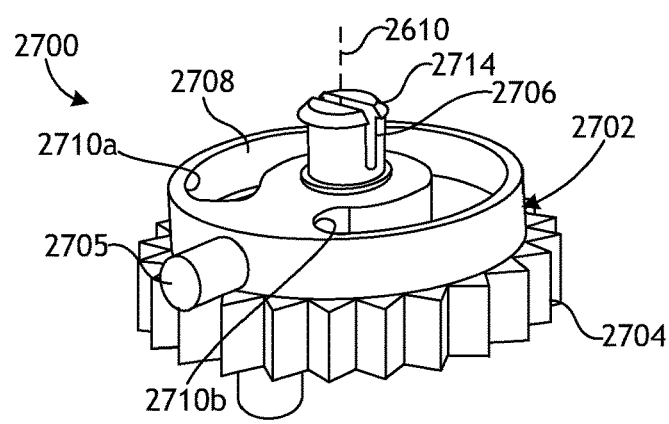
FIGS. 27A-27C are isometric views of an example dwell slip clutch structural component, according to one or more embodiments.
Figure 27B:
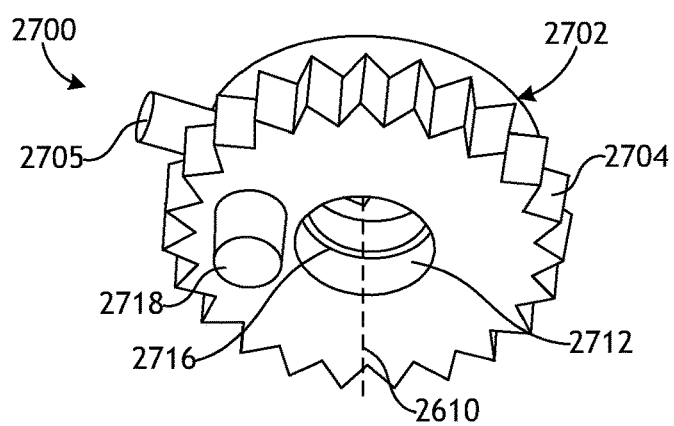
Figure 27C:
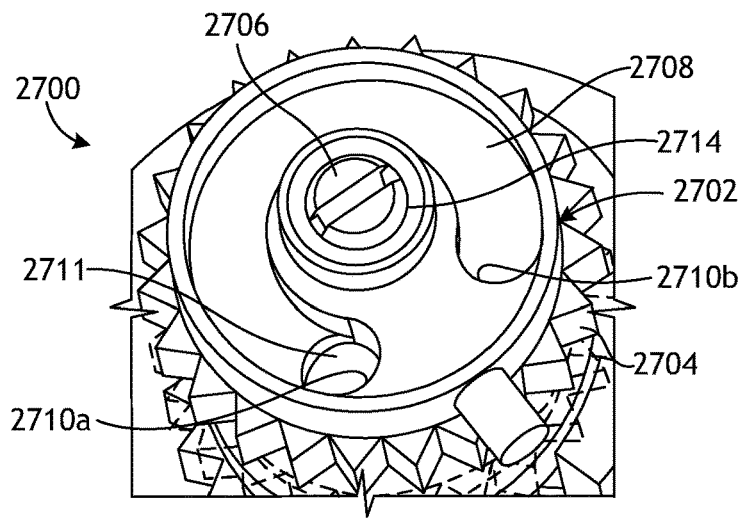

Referring briefly to FIGS. 27A-27C, illustrated are isometric views of an example dwell slip clutch structural component 2700, according to one or more embodiments. The dwell slip clutch structural component 2700 (hereafter the "component 2700") may be representative of one or more of the input and output clutch gears 2604, 2608 and the dwell disk 2606 shown in FIG. 26. Accordingly, discussion of the component 2700 may be applicable to any or all of the input and output clutch gears 2604, 2608 and the dwell disk 2606.

As illustrated, the component 2700 may comprise a generally disk-shaped body 2702 that provides gear teeth 2704 defined about its outer periphery (circumference). A radial pin 2705 may extend radially outward from the body 2702 and perpendicular to the common axis 2610. When the component 2700 is used as the dwell disk 2606, the gear teeth 2704 and the radial pin 2705 may be omitted. Moreover, the radial pin 2705 may only be needed when the component 2700 is used as the output clutch gear 2608, and therefore may be omitted on the input clutch gear 2604 and/or the dwell disk 2606.

As seen in FIGS. 27A and 27C, the top of the body 2702 may define a central extension 2706 that extends axially along and concentric with the common axis 2610. A closed-ended arcuate channel 2708 may also be defined in the body 2702 and partially circumscribe the central extension 2706. The arcuate channel 2708 terminates in a first end wall 2710a and an opposing second end wall 2710b. A depression or pocket 2711 may be defined in the arcuate channel 2708 at the first end wall 2710a, as best seen in FIG. 27C. Although contiguous with the channel 2708, the pocket 2711 may be inset into the body 2702 to a depth that is deeper than the arcuate channel 2708.

As seen in FIG. 27B, the bottom of the body 2702 defines a central aperture 2712 concentric with or aligned with the common axis 2610. When the input and output clutch gears 2604, 2608 and the dwell disk 2606 are stacked atop one another, as shown in FIG. 26, the central extension 2706 may be configured to be at least partially received within the central aperture 2712 of the component arranged directly above. In some embodiments, the central extension 2706 may be configured to be releasably coupled to the opposing central aperture 2712. In such embodiments, the central extension 2706 may provide or otherwise define a releasable coupling 2714 configured to mate with a corresponding matable feature 2716 provided within the central aperture 2712. In the illustrated embodiment, the releasable coupling 2714 comprises a snap-fit or collet feature, and the matable feature 2716 comprises a groove configured to receive the snap-fit feature and thereby releasably coupled upper and lower components together. Those skilled in the art will readily appreciate that the releasable coupling 2714 and the matable feature 2716 may be configured in other releasable designs and configurations, without departing from the scope of the disclosure.

The bottom of the body 2702 may also define an axial drive pin 2718 that extends eccentric to but parallel with the common axis 2610. When the input and output clutch gears 2604, 2608 and the dwell disk 2606 are stacked atop one another, as shown in FIG. 26, the axial drive pin 2718 of an upper component may be configured to be received within the arcuate channel 2708 of the component located directly below. Moreover, when moved to the first end wall 2710a, the axial drive pin 2718 may be axial aligned with and capable of being received within the pocket 2711. When the axial drive pin 2718 of an upper component is received within the pocket 2711 of a lower component, the two components will be able to rotate in unison and otherwise as a single component.

Referring again to FIG. 26, with continued reference to FIGS. 27A-27C, the dwell disk 2606 is mounted above the output clutch gear 2608 such that the axial drive pin 2718 of the dwell disk 2606 is received within the arcuate slot 2708 of the output clutch gear 2608. Similarly, the input clutch gear 2604 is mounted above the dwell disk 2606 such that the axial drive pin 2718 of the input clutch gear 2604 is received within the arcuate slot 2708 of the dwell disk 2606. The dwell slip clutch 2602 may be movable between a "collapsed" state and an "expanded" state, and the dwell slip clutch 2602 is depicted in FIG. 26 in the collapsed state. In the collapsed state, the axial drive pin 2718 of the dwell disk 2606 is received within the pocket 2711 of the output clutch gear 2608, and the axial drive pin 2718 of the input clutch gear 2604 is received within the pocket 2711 of the dwell disk 2606. With the axial drive pins 2718 received within the pockets 2711, this allows the entire dwell slip clutch 2602 to rotate in unison as the input clutch gear 2608 is rotated. In other words, when the axial drive pins 2718 are received within the pockets 2711, the stacked gears are rotationally keyed together with no dwell, thus creating direct input-output motion.

Moreover, in the collapsed state, the central extension 2706 of the dwell disk 2606 is releasably coupled to the central aperture 2712 of the input clutch gear 2604, and the central extension 2706 of the output clutch gear 2608 is releasably coupled to the central aperture 2712 of the dwell disk 2606.

Figure 28:
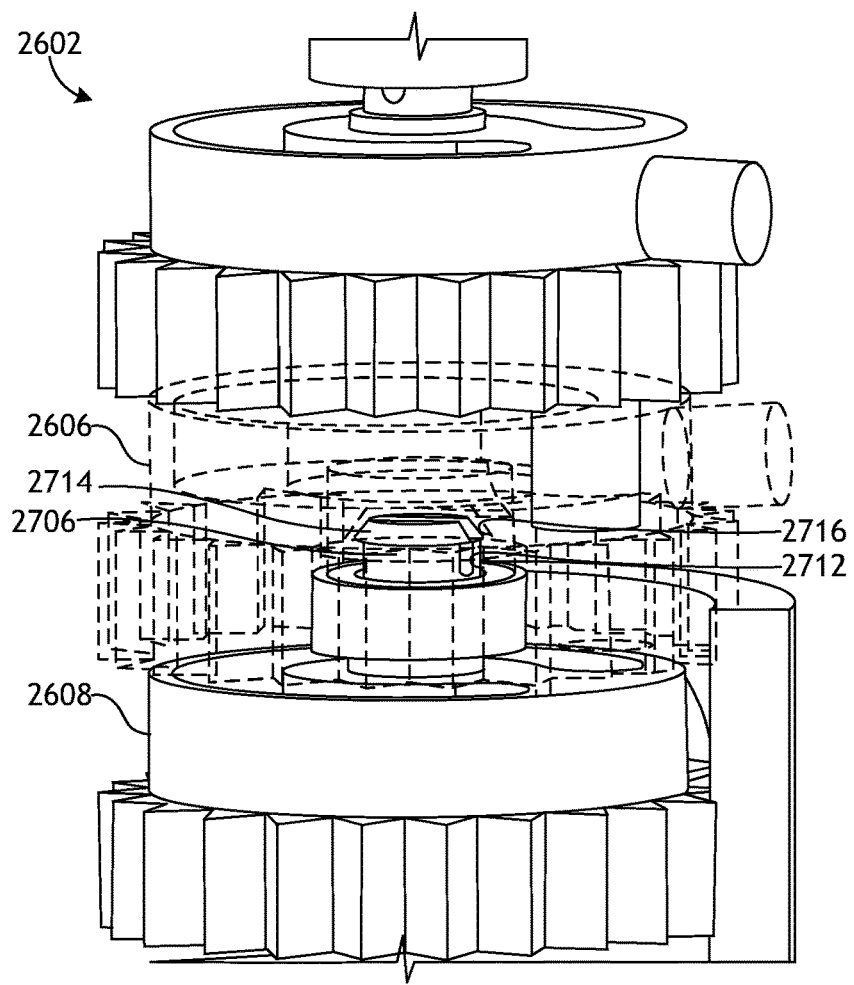
FIG. 28 is an enlarged side view of the dwell slip clutch of FIG. 26 in the collapsed state, according to one or more embodiments.

Referring briefly to FIG. 28, illustrated is an enlarged side view of the dwell slip clutch 2602 in the collapsed state. The dwell disk 2606 is shown in phantom (dashed lines) in FIG. 28 to enable viewing of the internal components. In the collapsed state, the central extension 2706 of the output clutch gear 2608 is releasably coupled to the central aperture 2712 of the dwell disk 2606. Moreover, the releasable coupling 2714 defined on the central extension 2706 is mated with the matable feature 2716 provided within the central aperture 2712 of the dwell disk 2706.

Referring again to FIG. 26, as illustrated, the radial pin 2705 of the output clutch gear 2608 may be received within an arcuate barrel cam 2612 defined in a member 2614 that forms part of or otherwise extends from the housing 2202. As the output clutch gear 2608 rotates, the radial pin 2705 will traverse the barrel cam 2612, which may define a vertical drop or dip 2616. When the radial pin 2705 descends into the vertical dip 2616, the dwell slip clutch 2602 may transition from the collapsed state to the expended state, as described below.

Example operation of the dwell slip clutch 2602 is now provided with reference to FIGS. 26 and FIGS. 27A-27C. With the dwell slip clutch 2602 in the collapsed state, as shown in FIG. 26, the input clutch gear 2604 may be rotated in a first angular direction D (e.g., clockwise), as acted upon (either directly or indirectly) by the insertion transmission gear 2212 (FIG. 22A). Since the axial drive pins 2718 are received within the pockets 2711, rotating the input clutch gear 2604 will simultaneously cause the dwell disk 2606 and the output clutch gear 2608 to also rotate in the first angular direction D. Rotating the output clutch gear 2608 will drive against the lockout ring 2222 (FIGS. 22A-22B and 23) to angularly misalign the tabs 2228 (FIGS. 22A-22B) with the slots 2226 (FIGS. 22A-22B), thus preventing the latch ring 2220 (FIGS. 22A-22B) from moving axially to the unlocked position.

Moreover, as the output clutch gear 2608 rotates in the first angular direction D, the radial pin 2705 provided by the output clutch gear 2608 will traverse the barrel cam 2612. When the radial pin 2705 descends into the vertical dip 2616, the dwell slip clutch 2602 may transition from the collapsed state to the expanded state. More specifically, the input clutch gear 2604 may be vertically fixed to a portion of the housing 2202, such as a portion of the top housing 2502 (FIGS. 25A-25B). As the radial pin 2705 enters the vertical dip 2616, the output clutch gear 2608 correspondingly drops vertically, which causes the output clutch gear 2608 to vertically separate from the dwell disk 2606, and further causes the dwell disk 2606 to vertically separate from the input clutch gear 2604, which remains vertically stationary.

Figure 29:
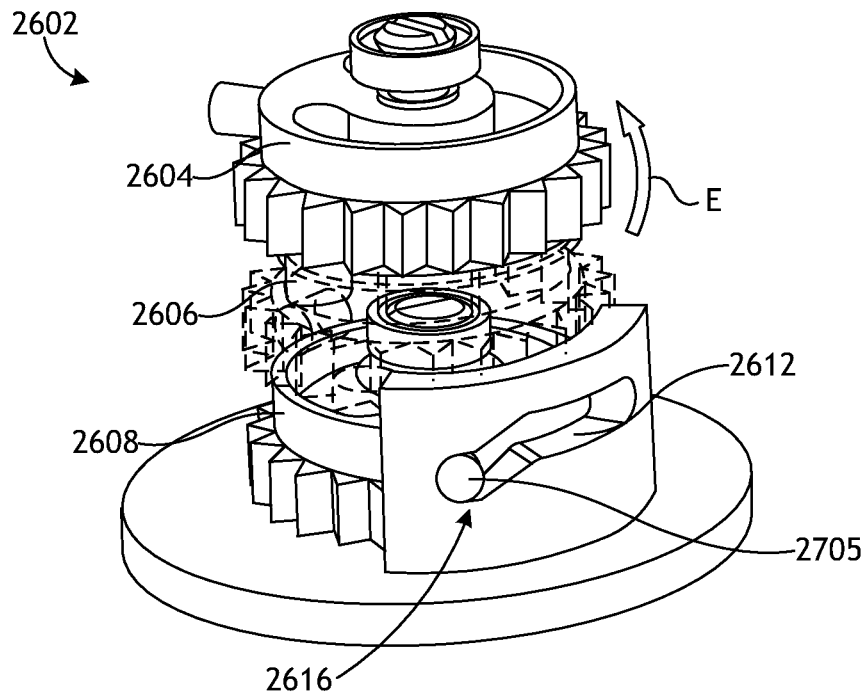
FIGS. 29 and 30 are isometric side and enlarged views, respectively, of the dwell slip clutch of FIG. 26 in the expanded state, according to one or more embodiments.
Figure 30:
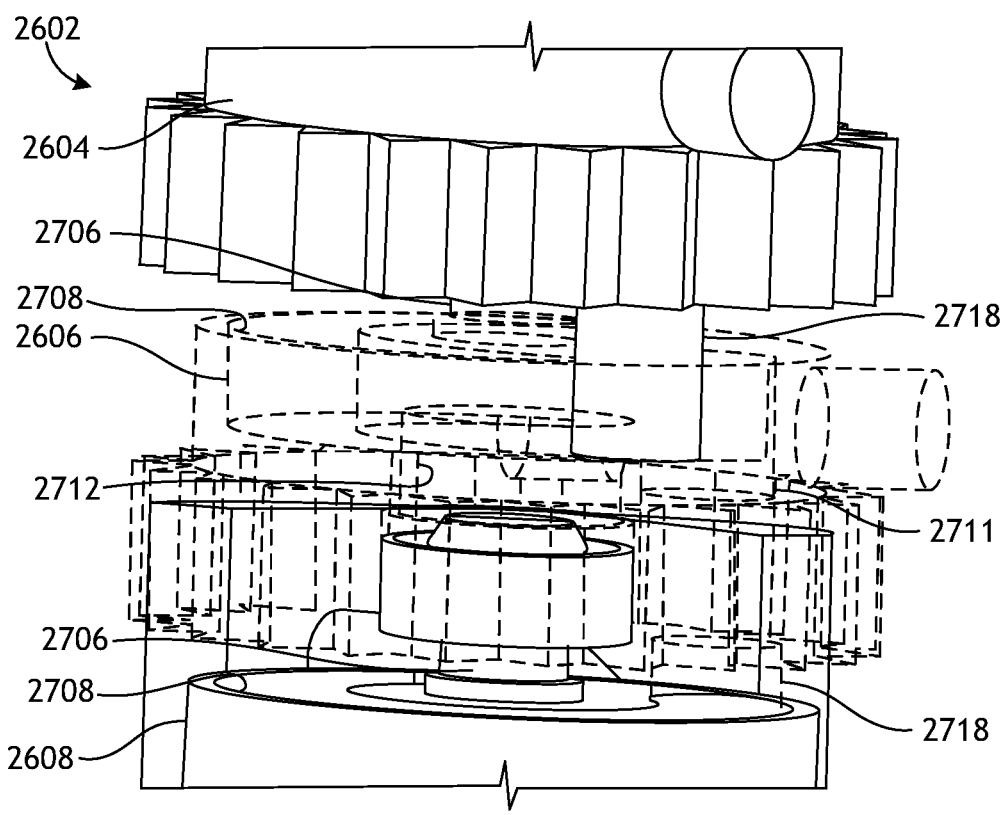

Referring now to FIGS. 29 and 30, illustrated are isometric side and enlarged views, respectively, of the dwell slip clutch 2602 moved to the expanded state, according to one or more embodiments. The dwell disk 2606 is shown in phantom (dashed lines) in FIGS. 29 and 30 to enable viewing of the internal components. As shown in FIG. 29, the radial pin 2705 of the output clutch gear 2608 has descended into the vertical dip 2616 of the barrel cam 2612, which causes the output clutch gear 2608 to correspondingly drop vertically and transition the dwell slip clutch 2602 to the expanded state. As shown in FIG. 30, transitioning the dwell slip clutch 2602 to the expanded state causes the central extension 2706 of the output clutch gear 2608 to be released from the central aperture 2712 of the dwell disk 2606. While not completely visible in FIG. 30, transitioning the dwell slip clutch 2602 to the expanded state also causes the central extension 2706 of the dwell disk 2606 to be released from the central aperture 2712 of the input clutch gear 2604.

Moreover, transitioning the dwell slip clutch 2602 to the expanded state also causes the axial drive pin 2718 of the input clutch gear 2604 to separate from the pocket 2711 of the dwell disk 2606, and further causes the axial drive pin 2718 of the dwell disk 2606 to separate from the pocket 2711 (not visible) of the output clutch gear 2608. This allows the axial drive pins 2718 to traverse freely within the adjacent arcuate channels 2708, and this ensures that no output motion from the output clutch gear 2608 is created after the vertical disengagement despite the amount of input motion from the input clutch gear 2610. In some embodiments, for example, the arc length of the arcuate channels 2708 is dimensioned such that a full insertion stroke will not bottom-out each of the axial drive pins 2718 as the dwell slip clutch 2602 rotates in the first angular direction D. Rather, the axial drive pins 2718 can traverse or "dwell" in the corresponding arcuate channels 2708 without driving the output clutch gear 2608. Accordingly, rotating the dwell slip clutch 2602 a predetermined angular distance (amount) can effectively disengage the output clutch gear 2608, such that no additional parasitic drag is added to the system during normal insertion of the device and until the dwell slip clutch 2602 is rotated in the opposite direction to reengage the output clutch gear 2608.

Still referring to FIGS. 29 and 30, to transition the dwell slip clutch 2602 back to the collapsed state, the input clutch gear 2604 may be rotated in a second angular direction E, opposite the first angular direction D. As described above, rotating the input clutch gear 2604 is done via insertion and operation of the insertion assembly 2208 (FIG. 22A). This will cause the axial drive pin 2718 of the input clutch gear 2604 to traverse the arcuate channel 2708 of the dwell disk 2606 until bottoming out against the first end wall 2710a (FIG. 27C) where the corresponding pocket 2711 is located. Upon bottoming out against the first end wall 2710a of the dwell disk 2606, further rotation of the input clutch gear 2604 in the second angular direction E will cause the dwell disk 2606 to also rotate in the second angular direction E. This will cause the axial drive pin 2718 of the dwell disk 2606 to traverse the arcuate channel 2708 of the output clutch gear 2608 until bottoming out against the first end wall 2710a (FIG. 27C) where the corresponding pocket 2711 is located. Upon bottoming out against the first end wall 2710a of the output clutch gear 2608, further rotation of the input clutch gear 2604 in the second angular direction E will cause the output clutch gear 2608 to also rotate in the second angular direction E.

As the output clutch gear 2608 rotates in the second angular direction E, the output clutch gear 2608 will drive against the lockout ring 2222 (FIGS. 22A-22B and 23) to angularly align the tabs 2228 (FIGS. 22A-22B) with the slots 2226 (FIGS. 22A-22B), thus allowing the latch ring 2220 (FIGS. 22A-22B) to be moved axially to the unlocked position. Moving the clutch gear 2608 in the second angular direction E also causes the radial pin 2705 of the output clutch gear 2608 to traverse the barrel cam 2612 and migrate out of the vertical dip 2616. Moving the radial pin 2705 out of the vertical dip 2616 transitions the dwell slip clutch 2602 back to the collapsed state as the stacked gears are vertically compressed. More specifically, as the radial pin 2705 moves (traverses) out of the vertical dip 2616, the output clutch gear 2608 correspondingly moves vertically upward, which drives the output clutch gear 2608 vertically towards the dwell disk 2606, and further drives the dwell disk 2606 vertically toward the input clutch gear 2604, which remains vertically stationary. In this position, where the axial drive pins 2718 are bottomed out and positioned vertically above the corresponding pockets 2711, the dwell slip clutch 2602 can collapse into the collapsed state, which resets the dwell slip clutch 2602 to be ready for the next insertion.

A desired output is to have a small amount of rotation of the output clutch gear 2608 in the first angular direction D (FIG. 26) at the beginning, then have the "dwell" effectively act as a slip clutch, allowing additional input motion in the first angular direction D, without additional output motion. Then, when the input is driven fully in the first angular direction D. The output clutch gear 2608 can then be driven in the second angular direction E at the final amount of rotation, and any rotation motion of the dwell slip clutch 2602 occurring in between these points would be input motion, and possibly idler motion, but no output motion. Additionally, the design may incorporate additional dwell disks 2606 interposing the input and output clutch gears 2604, 2608 to create additional "dwell" time.

Embodiments Disclosed Herein Include

A. A robotic surgical tool that includes a handle and an instrument driver releasably coupled to the handle, an elongate shaft extendable through the handle and the instrument driver, and a decoupler interposing the handle and the instrument driver and including an insertion assembly rotatably mounted to a decoupler housing and actuatable to move the shaft axially relative to the handle and the instrument driver, an insertion transmission gear operatively coupled to and driven by the insertion assembly, and a dwell slip clutch rotatably mounted to the decoupler housing and including an input clutch gear and an output clutch gear, the input clutch gear being operatively coupled to the insertion transmission gear such that rotation of the insertion transmission gear drives the input clutch gear, wherein the dwell slip clutch is movable between a collapsed state, where the input clutch gear directly drives the output clutch gear, and an expanded state, where the input clutch gear is rotatable relative to the output clutch gear. The robotic surgical tool further including a lockout ring extending about the decoupler housing and engageable with the output clutch gear, and a latch ring extending about the decoupler housing and axially offset from the lockout ring, wherein fully retracting the shaft moves the dwell slip clutch to the compressed state to drive the output clutch gear against the lockout ring and thereby angularly align the latch ring with the lockout ring, and wherein, when the latch ring is angularly aligned with the lockout ring, the latch ring is movable to an unlocked position that separates the handle from the instrument driver.

B. A method of operating a robotic surgical tool that includes releasably coupling a handle of the robotic surgical tool to an instrument driver, the robotic surgical tool including an elongate shaft extendable through the handle and the instrument driver, a decoupler interposing the handle and the instrument driver and including an insertion assembly rotatably mounted to a decoupler housing, an insertion transmission gear operatively coupled to and driven by the insertion assembly, and a dwell slip clutch rotatably mounted to the decoupler housing and including an input clutch gear and an output clutch gear, the input clutch gear being operatively coupled to the insertion transmission gear, a lockout ring extending about the decoupler housing and engageable with the output clutch gear, and a latch ring extending about the decoupler housing and axially offset from the lockout ring. The method further including actuating the insertion assembly and thereby moving the shaft axially relative to the handle and the instrument driver, driving the dwell slip clutch via actuation of the insertion assembly, the dwell slip clutch being movable between a collapsed state, where the input clutch gear directly drives the output clutch gear, and an expanded state, where the input clutch gear is rotatable relative to the output clutch gear, retracting the shaft and thereby transitioning the dwell slip clutch to the compressed state where the output clutch gear drives against the lockout ring, rotating the lockout ring with the output cutch gear and thereby angularly aligning the lockout ring with latch ring, and moving the latch ring to an unlocked position once the latch ring is angularly aligned with the lockout ring, and thereby separating the handle from the instrument driver.

Each of embodiments A and B may have one or more of the following additional elements in any combination: Element 1: further comprising one or more slots defined on one of the latch ring and the lockout ring, and one or more tabs defined on the other of the latch ring and the lockout ring, wherein driving the output clutch gear against the lockout ring angularly aligns or misaligns the one or more slots with the one or more tabs, the latch ring being movable to the unlocked position when the one or more slots are aligned with the one or more tabs. Element 2: wherein the lockout ring defines a sector gear engageable with the output clutch gear. Element 3: wherein the dwell slip clutch further includes a driven gear mounted to an axle and arranged to interface with the insertion transmission gear, and a pinion gear mounted to the axle and arranged to interface with the input clutch gear, wherein rotation of the insertion transmission gear correspondingly rotates the driven gear, the pinion gear, and the input clutch gear. Element 4: wherein the input and output clutch gears are rotatably mounted to a common axle, the dwell slip clutch further including a dwell disk rotatably mounted to the common axle and axially interposing the input and output clutch gears, a first spring arranged between the input clutch gear and the dwell disk, and a second spring arranged between the dwell disk and the output clutch gear, wherein the first and second springs naturally bias the dwell slip clutch to the expanded state. Element 5: wherein the dwell slip clutch further includes a first axial drive pin defined on an upper surface of the input clutch gear and arranged to laterally engage a first raised shoulder defined on an opposing bottom surface of the dwell disk, and a second axial drive pin defined on an upper surface of the dwell disk and arranged to laterally engage a second raised shoulder defined on an opposing bottom surface of the output clutch gear, wherein, when the dwell slip clutch is in the expanded state, the first and second axial drive pins are movable relative to the adjacent first and second raised shoulders. Element 6: wherein the dwell slip clutch further includes a first pocket defined in the opposing bottom surface of the dwell disk adjacent the first raised shoulder, and a second pocket defined in the opposing bottom surface of the output clutch gear adjacent the second raised shoulder, wherein, when the dwell slip clutch is moved to the collapsed state, the first and second axial drive pins are received within the first and second pockets, respectively. Element 7: wherein the decoupler further includes a top housing mounted to the decoupler housing, the top housing providing a first ramp defined on a bottom surface of the top housing, and the dwell slip clutch further includes a second ramp defined on a top surface of the output clutch gear and engageable with the first ramp, wherein rotating the dwell slip clutch in a first angular direction slidably engages the second ramp against the first ramp and thereby transitions the dwell slip clutch from the expanded state to the collapsed state, and wherein rotating the dwell slip clutch in a second angular direction opposite the first angular direction disengages the second ramp from the first ramp and thereby allows the first and second springs to transition the dwell slip clutch from the collapsed state to the expanded. Element 8: wherein the input and output clutch gears are aligned along a common axis, the dwell slip clutch further including a dwell disk rotatably aligned along the common axis and axially interposing the input and output clutch gears, a radial pin extending radially outward from the output clutch gear, and a barrel cam defined in the decoupler housing and sized to receive the radial pin, the barrel cam providing a vertical dip, wherein, when the radial pin descends into the vertical dip as the output clutch gear rotates, the dwell slip clutch transitions from the collapsed state to the expended state. Element 9: wherein the dwell slip clutch further includes a first central extension extending from a top surface of the output clutch gear and along the common axis, a first central aperture defined in a bottom surface of the dwell disk and aligned with the first central extension, a second central extension extending from a top surface of the dwell disk and along the common axis, and a second central aperture defined in a bottom surface of the input clutch gear and aligned with the second central extension, wherein, when the dwell slip clutch transitions to the collapsed state, the first and second central extensions are received within and releasably coupled to the first and second central apertures, respectively. Element 10: wherein the first and second central extensions provide a releasable coupling matable with a corresponding matable feature provided within the first and second central apertures, respectively. Element 11: wherein the dwell slip clutch further includes a first arcuate channel defined in a top surface of the output clutch gear, a first axial drive pin extending from a bottom surface of the dwell disk and receivable within the first arcuate channel, a second arcuate channel defined in a top surface of the dwell disk, and a second axial drive pin extending from a bottom surface of the input clutch gear and receivable within the second arcuate channel, wherein, when the dwell slip clutch is in the expanded state, the first and second axial drive pins are translatable within the first and second arcuate channels, respectively. Element 12: wherein the dwell slip clutch further includes a first pocket defined in the first arcuate channel, and a second pocket defined in the second arcuate channel, wherein, when the dwell slip clutch is in the collapsed state, the first and second axial drive pins are received within the first and second pockets, respectively.

Element 13: wherein one or more slots are defined on one of the latch ring and the lockout ring, and one or more tabs are defined on the other of the latch ring and the lockout ring, and wherein rotating the lockout ring with the output cutch gear further comprises driving the output clutch gear against the lockout ring to angularly align the one or more slots with the one or more tabs. Element 14: wherein the input and output clutch gears are rotatably mounted to a common axle and the dwell slip clutch further includes a dwell disk rotatably mounted to the common axle and axially interposing the input and output clutch gears, a first spring arranged between the input clutch gear and the dwell disk, and a second spring arranged between the dwell disk and the output clutch gear, the method further comprising naturally biasing the dwell slip clutch to the expanded state with the first and second springs. Element 15: wherein the dwell slip clutch further includes a first axial drive pin defined on an upper surface of the input clutch gear and arranged to laterally engage a first raised shoulder defined on an opposing bottom surface of the dwell disk, and a second axial drive pin defined on an upper surface of the dwell disk and arranged to laterally engage a second raised shoulder defined on an opposing bottom surface of the output clutch gear, the method further comprising moving the first and second axial drive pins relative to the adjacent first and second raised shoulders, respectively, when the dwell slip clutch is in the expanded state. Element 16: wherein the dwell slip clutch further includes a first pocket defined in the opposing bottom surface of the dwell disk adjacent the first raised shoulder, and a second pocket defined in the opposing bottom surface of the output clutch gear adjacent the second raised shoulder, the method further comprising receiving the first and second axial drive pins within the first and second pockets, respectively, when the dwell slip clutch is moved to the collapsed state. Element 17: wherein the decoupler further includes a top housing mounted to the decoupler housing, the top housing providing a first ramp defined on a bottom surface of the top housing, and the dwell slip clutch further includes a second ramp defined on a top surface of the output clutch gear and engageable with the first ramp, the method further comprising rotating the dwell slip clutch in a first angular direction and thereby slidably engaging the second ramp against the first ramp to transition the dwell slip clutch from the expanded state to the collapsed state, rotating the dwell slip clutch in a second angular direction opposite the first angular direction and thereby disengaging the second ramp from the first ramp, and transitioning the dwell slip clutch from the collapsed state to the expanded with the first and second springs. Element 18: wherein the input and output clutch gears are aligned along a common axis, the dwell slip clutch further including a dwell disk rotatably aligned along the common axis and axially interposing the input and output clutch gears, a radial pin extending radially outward from the output clutch gear, and a barrel cam defined in the decoupler housing and sized to receive the radial pin, the barrel cam providing a vertical dip, wherein the method further comprises rotating the output clutch gear and thereby translating the radial pin within the barrel cam, and transitioning the dwell slip clutch from the collapsed state to the expended state as the radial pin moves into the vertical dip. Element 19: wherein the dwell slip clutch further includes a first central extension extending from a top surface of the output clutch gear and along the common axis, a first central aperture defined in a bottom surface of the dwell disk and aligned with the first central extension, a second central extension extending from a top surface of the dwell disk and along the common axis, and a second central aperture defined in a bottom surface of the input clutch gear and aligned with the second central extension, the method further comprising receiving and releasably coupling the first and second central extensions within the first and second central apertures, respectively, when the dwell slip clutch transitions to the collapsed state. Element 20: wherein the dwell slip clutch further includes a first arcuate channel defined in a top surface of the output clutch gear, a first axial drive pin extending from a bottom surface of the dwell disk and receivable within the first arcuate channel, a second arcuate channel defined in a top surface of the dwell disk, and a second axial drive pin extending from a bottom surface of the input clutch gear and receivable within the second arcuate channel, the method further comprising translating the first and second axial drive pins within the first and second arcuate channels, respectively, when the dwell slip clutch is in the expanded state. Element 21: wherein the dwell slip clutch further includes a first pocket defined in the first arcuate channel, and a second pocket defined in the second arcuate channel, the method further comprising receiving the first and second axial drive pins within the first and second pockets, respectively, when the dwell slip clutch is in the collapsed state.

By way of non-limiting example, exemplary combinations applicable to A and B include: Element 4 with Element 5; Element 5 with Element 6; Element 4 with Element 7; Element 8 with Element 9; Element 9 with Element 10; Element 8 with Element 11; Element 11 with Element 12; Element 14 with Element 15; Element 15 with Element 16; Element 14 with Element 17; Element 18 with Element 19; Element 18 with Element 20; and Element 20 with Element 21.

3. Implementing Systems and Terminology.

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification, which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
    a handle and an instrument driver releasably coupled to the handle;
    an elongate shaft extendable through the handle and the instrument driver; and
    a decoupler interposing the handle and the instrument driver and including:
        an insertion assembly rotatably mounted to a decoupler housing and actuatable to move the shaft axially relative to the handle and the instrument driver;
        an insertion transmission gear operatively coupled to and driven by the insertion assembly; and
        a dwell slip clutch rotatably mounted to the decoupler housing and including an input clutch gear and an output clutch gear, the input clutch gear being operatively coupled to the insertion transmission gear such that rotation of the insertion transmission gear drives the input clutch gear, wherein the dwell slip clutch is movable between a collapsed state, where the input clutch gear directly drives the output clutch gear, and an expanded state, where the input clutch gear is rotatable relative to the output clutch gear;
    a lockout ring extending about the decoupler housing and engageable with the output clutch gear; and
    a latch ring extending about the decoupler housing and axially offset from the lockout ring,
    wherein fully retracting the shaft moves the dwell slip clutch to the compressed state to drive the output clutch gear against the lockout ring and thereby angularly align the latch ring with the lockout ring, and wherein, when the latch ring is angularly aligned with the lockout ring, the latch ring is movable to an unlocked position that separates the handle from the instrument driver.

2. The robotic surgical tool of claim 1, further comprising:
    one or more slots defined on one of the latch ring and the lockout ring; and
    one or more tabs defined on the other of the latch ring and the lockout ring,
    wherein driving the output clutch gear against the lockout ring angularly aligns or misaligns the one or more slots with the one or more tabs, the latch ring being movable to the unlocked position when the one or more slots are aligned with the one or more tabs.

3. The robotic surgical tool of claim 1, wherein the lockout ring defines a sector gear engageable with the output clutch gear.

4. The robotic surgical tool of claim 1, wherein the dwell slip clutch further includes:
    a driven gear mounted to an axle and arranged to interface with the insertion transmission gear; and
    a pinion gear mounted to the axle and arranged to interface with the input clutch gear, wherein rotation of the insertion transmission gear correspondingly rotates the driven gear, the pinion gear, and the input clutch gear.

5. The robotic surgical tool of claim 1, wherein the input and output clutch gears are rotatably mounted to a common axle, the dwell slip clutch further including:
    a dwell disk rotatably mounted to the common axle and axially interposing the input and output clutch gears;
    a first spring arranged between the input clutch gear and the dwell disk; and
    a second spring arranged between the dwell disk and the output clutch gear, wherein the first and second springs naturally bias the dwell slip clutch to the expanded state.

6. The robotic surgical tool of claim 5, wherein the dwell slip clutch further includes:
    a first axial drive pin defined on an upper surface of the input clutch gear and arranged to laterally engage a first raised shoulder defined on an opposing bottom surface of the dwell disk; and
    a second axial drive pin defined on an upper surface of the dwell disk and arranged to laterally engage a second raised shoulder defined on an opposing bottom surface of the output clutch gear,
    wherein, when the dwell slip clutch is in the expanded state, the first and second axial drive pins are movable relative to the adjacent first and second raised shoulders.

7. The robotic surgical tool of claim 6, wherein the dwell slip clutch further includes:
    a first pocket defined in the opposing bottom surface of the dwell disk adjacent the first raised shoulder; and
    a second pocket defined in the opposing bottom surface of the output clutch gear adjacent the second raised shoulder,
    wherein, when the dwell slip clutch is moved to the collapsed state, the first and second axial drive pins are received within the first and second pockets, respectively.

8. The robotic surgical tool of claim 5, wherein the decoupler further includes a top housing mounted to the decoupler housing, the top housing providing a first ramp defined on a bottom surface of the top housing, and the dwell slip clutch further includes a second ramp defined on a top surface of the output clutch gear and engageable with the first ramp,
- wherein rotating the dwell slip clutch in a first angular direction slidably engages the second ramp against the first ramp and thereby transitions the dwell slip clutch from the expanded state to the collapsed state, and
- wherein rotating the dwell slip clutch in a second angular direction opposite the first angular direction disengages the second ramp from the first ramp and thereby allows the first and second springs to transition the dwell slip clutch from the collapsed state to the expanded.

9. The robotic surgical tool of claim 1, wherein the input and output clutch gears are aligned along a common axis, the dwell slip clutch further including:
- a dwell disk rotatably aligned along the common axis and axially interposing the input and output clutch gears;
- a radial pin extending radially outward from the output clutch gear; and
- a barrel cam defined in the decoupler housing and sized to receive the radial pin, the barrel cam providing a vertical dip,
- wherein, when the radial pin descends into the vertical dip as the output clutch gear rotates, the dwell slip clutch transitions from the collapsed state to the expended state.

10. The robotic surgical tool of claim 9, wherein the dwell slip clutch further includes:
- a first central extension extending from a top surface of the output clutch gear and along the common axis;
- a first central aperture defined in a bottom surface of the dwell disk and aligned with the first central extension;
- a second central extension extending from a top surface of the dwell disk and along the common axis; and
- a second central aperture defined in a bottom surface of the input clutch gear and aligned with the second central extension,
- wherein, when the dwell slip clutch transitions to the collapsed state, the first and second central extensions are received within and releasably coupled to the first and second central apertures, respectively.

11. The robotic surgical tool of claim 10, wherein the first and second central extensions provide a releasable coupling matable with a corresponding matable feature provided within the first and second central apertures, respectively.

12. The robotic surgical tool of claim 9, wherein the dwell slip clutch further includes:
- a first arcuate channel defined in a top surface of the output clutch gear;
- a first axial drive pin extending from a bottom surface of the dwell disk and receivable within the first arcuate channel;
- a second arcuate channel defined in a top surface of the dwell disk; and
- a second axial drive pin extending from a bottom surface of the input clutch gear and receivable within the second arcuate channel,
- wherein, when the dwell slip clutch is in the expanded state, the first and second axial drive pins are translatable within the first and second arcuate channels, respectively.

13. The robotic surgical tool of claim 12, wherein the dwell slip clutch further includes:
- a first pocket defined in the first arcuate channel; and
- a second pocket defined in the second arcuate channel,
- wherein, when the dwell slip clutch is in the collapsed state, the first and second axial drive pins are received within the first and second pockets, respectively.

14. A method of operating a robotic surgical tool, comprising:
- releasably coupling a handle of the robotic surgical tool to an instrument driver, the robotic surgical tool including:
  - an elongate shaft extendable through the handle and the instrument driver;
  - a decoupler interposing the handle and the instrument driver and including an insertion assembly rotatably mounted to a decoupler housing, an insertion transmission gear operatively coupled to and driven by the insertion assembly, and a dwell slip clutch rotatably mounted to the decoupler housing and including an input clutch gear and an output clutch gear, the input clutch gear being operatively coupled to the insertion transmission gear;
  - a lockout ring extending about the decoupler housing and engageable with the output clutch gear; and
  - a latch ring extending about the decoupler housing and axially offset from the lockout ring;
- actuating the insertion assembly and thereby moving the shaft axially relative to the handle and the instrument driver;
- driving the dwell slip clutch via actuation of the insertion assembly, the dwell slip clutch being movable between a collapsed state, where the input clutch gear directly drives the output clutch gear, and an expanded state, where the input clutch gear is rotatable relative to the output clutch gear;
- retracting the shaft and thereby transitioning the dwell slip clutch to the compressed state where the output clutch gear drives against the lockout ring;
- rotating the lockout ring with the output cutch gear and thereby angularly aligning the lockout ring with latch ring; and
- moving the latch ring to an unlocked position once the latch ring is angularly aligned with the lockout ring, and thereby separating the handle from the instrument driver.

15. The method of claim 14, wherein one or more slots are defined on one of the latch ring and the lockout ring, and one or more tabs are defined on the other of the latch ring and the lockout ring, and wherein rotating the lockout ring with the output cutch gear further comprises driving the output clutch gear against the lockout ring to angularly align the one or more slots with the one or more tabs.

16. The method of claim 14, wherein the input and output clutch gears are rotatably mounted to a common axle and the dwell slip clutch further includes a dwell disk rotatably mounted to the common axle and axially interposing the input and output clutch gears, a first spring arranged between the input clutch gear and the dwell disk, and a second spring arranged between the dwell disk and the output clutch gear, the method further comprising:
- naturally biasing the dwell slip clutch to the expanded state with the first and second springs.

17. The method of claim 16, wherein the dwell slip clutch further includes a first axial drive pin defined on an upper surface of the input clutch gear and arranged to laterally engage a first raised shoulder defined on an opposing bottom surface of the dwell disk, and a second axial drive pin defined on an upper surface of the dwell disk and arranged to laterally engage a second raised shoulder defined on an opposing bottom surface of the output clutch gear, the method further comprising:

moving the first and second axial drive pins relative to the adjacent first and second raised shoulders, respectively, when the dwell slip clutch is in the expanded state.

18. The method of claim 17, wherein the dwell slip clutch further includes a first pocket defined in the opposing bottom surface of the dwell disk adjacent the first raised shoulder, and a second pocket defined in the opposing bottom surface of the output clutch gear adjacent the second raised shoulder, the method further comprising:

receiving the first and second axial drive pins within the first and second pockets, respectively, when the dwell slip clutch is moved to the collapsed state.

19. The method of claim 16, wherein the decoupler further includes a top housing mounted to the decoupler housing, the top housing providing a first ramp defined on a bottom surface of the top housing, and the dwell slip clutch further includes a second ramp defined on a top surface of the output clutch gear and engageable with the first ramp, the method further comprising:

rotating the dwell slip clutch in a first angular direction and thereby slidably engaging the second ramp against the first ramp to transition the dwell slip clutch from the expanded state to the collapsed state;

rotating the dwell slip clutch in a second angular direction opposite the first angular direction and thereby disengaging the second ramp from the first ramp; and transitioning the dwell slip clutch from the collapsed state to the expanded with the first and second springs.

20. The method of claim 14, wherein the input and output clutch gears are aligned along a common axis, the dwell slip clutch further including a dwell disk rotatably aligned along the common axis and axially interposing the input and output clutch gears, a radial pin extending radially outward from the output clutch gear, and a barrel cam defined in the decoupler housing and sized to receive the radial pin, the barrel cam providing a vertical dip, wherein the method further comprises:

rotating the output clutch gear and thereby translating the radial pin within the barrel cam; and transitioning the dwell slip clutch from the collapsed state to the expended state as the radial pin moves into the vertical dip.

21. The method of claim 20, wherein the dwell slip clutch further includes a first central extension extending from a top surface of the output clutch gear and along the common axis, a first central aperture defined in a bottom surface of the dwell disk and aligned with the first central extension, a second central extension extending from a top surface of the dwell disk and along the common axis, and a second central aperture defined in a bottom surface of the input clutch gear and aligned with the second central extension, the method further comprising:

receiving and releasably coupling the first and second central extensions within the first and second central apertures, respectively, when the dwell slip clutch transitions to the collapsed state.

22. The method of claim 20, wherein the dwell slip clutch further includes a first arcuate channel defined in a top surface of the output clutch gear, a first axial drive pin extending from a bottom surface of the dwell disk and receivable within the first arcuate channel, a second arcuate channel defined in a top surface of the dwell disk, and a second axial drive pin extending from a bottom surface of the input clutch gear and receivable within the second arcuate channel, the method further comprising:

translating the first and second axial drive pins within the first and second arcuate channels, respectively, when the dwell slip clutch is in the expanded state.

23. The method of claim 22, wherein the dwell slip clutch further includes a first pocket defined in the first arcuate channel, and a second pocket defined in the second arcuate channel, the method further comprising:

receiving the first and second axial drive pins within the first and second pockets, respectively, when the dwell slip clutch is in the collapsed state.

\* \* \* \* \*